United States Patent
Sharma et al.

(10) Patent No.: US 12,077,612 B2
(45) Date of Patent: Sep. 3, 2024

(54) PEPTIDE COMPOSITIONS

(71) Applicant: RHYTHM PHARMACEUTICALS, INC., Boston, MA (US)

(72) Inventors: Shubh Sharma, Cranbury, NJ (US); Leonardus H. T. Van Der Ploeg, Newton, MA (US); Bart Henderson, Belmont, MA (US)

(73) Assignee: RHYTHM PHARMACEUTICALS, INC., Boston, MA (US)

( * ) Notice: Subject to any disclaimer, the term of this patent is extended or adjusted under 35 U.S.C. 154(b) by 347 days.

(21) Appl. No.: 17/080,293

(22) Filed: Oct. 26, 2020

(65) Prior Publication Data

US 2021/0040155 A1    Feb. 11, 2021

Related U.S. Application Data

(60) Continuation of application No. 16/216,116, filed on Dec. 11, 2018, now Pat. No. 10,858,399, which is a division of application No. 14/775,916, filed as application No. PCT/US2014/028590 on Mar. 14, 2014, now Pat. No. 10,196,425.

(60) Provisional application No. 61/790,469, filed on Mar. 15, 2013.

(51) Int. Cl.
   *C07K 7/54*   (2006.01)
   *A61K 38/00*  (2006.01)
   *A61K 38/12*  (2006.01)
   *C07K 14/685* (2006.01)

(52) U.S. Cl.
   CPC ........... *C07K 7/54* (2013.01); *A61K 38/12* (2013.01); *C07K 14/685* (2013.01); *A61K 38/00* (2013.01)

(58) Field of Classification Search
   CPC ........ C07K 7/54; C07K 14/685; A61K 38/12; A61K 38/00; A61P 1/16; A61P 3/04; A61P 3/06; A61P 3/10; A61P 9/00; A61P 15/00; A61P 15/10; A61P 15/12; A61P 43/00
   See application file for complete search history.

(56) References Cited

U.S. PATENT DOCUMENTS

| | | | |
|---|---|---|---|
| 5,731,408 A | 3/1998 | Hadley et al. | |
| 7,342,089 B2 | 3/2008 | Sharma et al. | |
| 7,345,144 B2 | 3/2008 | Sharma et al. | |
| 7,368,433 B2 | 5/2008 | Haskell-Luevano et al. | |
| 8,039,435 B2 | 10/2011 | Dong et al. | |
| 8,343,031 B2* | 1/2013 | Gertner | A61B 17/1114 600/37 |
| 8,349,797 B2 | 1/2013 | Dong et al. | |
| 8,563,000 B2 | 10/2013 | Dong et al. | |
| 9,155,777 B2 | 10/2015 | Halem et al. | |
| 10,196,425 B2* | 2/2019 | Sharma | C07K 7/54 |
| 10,858,399 B2* | 12/2020 | Sharma | A61P 43/00 |
| 11,129,869 B2* | 9/2021 | Sharma | A61K 47/544 |
| 2005/0267147 A1 | 12/2005 | Poitout et al. | |
| 2006/0014194 A1 | 1/2006 | Sharma et al. | |
| 2006/0014676 A1 | 1/2006 | Sharma et al. | |
| 2006/0173036 A1 | 8/2006 | Poitout et al. | |
| 2006/0281784 A1 | 12/2006 | Poitout et al. | |
| 2006/0293223 A1 | 12/2006 | Gadski et al. | |
| 2007/0105759 A1 | 5/2007 | Flora et al. | |
| 2009/0209531 A1 | 8/2009 | Poitout et al. | |
| 2009/0305960 A1 | 12/2009 | Chen et al. | |
| 2010/0173834 A1 | 7/2010 | Dong | |
| 2010/0311648 A1 | 12/2010 | Dodd et al. | |
| 2012/0135923 A1 | 5/2012 | Halem et al. | |
| 2012/0225816 A1 | 9/2012 | Dong et al. | |
| 2012/0226018 A1 | 9/2012 | Dong | |
| 2014/0127303 A1 | 5/2014 | Richard et al. | |
| 2015/0157719 A1 | 6/2015 | Baronnet et al. | |

FOREIGN PATENT DOCUMENTS

| | | |
|---|---|---|
| CN | 101257916 A | 9/2008 |
| CN | 102458436 A | 5/2012 |
| EP | 0292291 A2 | 11/1988 |
| WO | 2000/035952 A2 | 6/2000 |
| WO | 2002/018437 A2 | 3/2002 |
| WO | 03006620 A2 | 1/2003 |
| WO | 2005/000338 A1 | 1/2005 |
| WO | 2005/000339 A2 | 1/2005 |
| WO | 2005014617 A2 | 2/2005 |
| WO | 2007/008704 A2 | 1/2007 |
| WO | 2008/147556 A2 | 12/2008 |
| WO | 2009/151383 A1 | 12/2009 |

(Continued)

OTHER PUBLICATIONS

Examination Report for Australian Application No. 2014227712 dated Jul. 20, 2017.

(Continued)

*Primary Examiner* — Marcela M Cordero Garcia

(74) *Attorney, Agent, or Firm* — Lando & Anastasi, LLP

(57) ABSTRACT

The present invention relates to polypeptide compounds that are modulators (e.g., agonists and antagonists) of the melanocortin-4 receptor (MC4R) and pharmaceutical compositions comprising same. The compounds described herein are polypeptide of the following structural Formula (I):

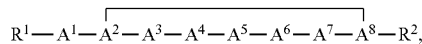

$$R^1 - A^1 - A^2 - A^3 - A^4 - A^5 - A^6 - A^7 - A^8 - R^2,$$

or a pharmaceutically acceptable salt thereof. Values and preferred values of the variables in structural Formula (I) are described herein.

6 Claims, No Drawings

Specification includes a Sequence Listing.

(56) References Cited

FOREIGN PATENT DOCUMENTS

| WO | 2010/144344 A2 | 12/2010 |
| WO | 2010144038 A1 | 12/2010 |
| WO | 2011/060352 A1 | 5/2011 |
| WO | 2011060355 A1 | 5/2011 |
| WO | 2014/144260 A1 | 9/2014 |
| WO | 2014/144842 A2 | 9/2014 |

OTHER PUBLICATIONS

Kontijevskis et al., "Proteochemometric analysis of small cyclic peptides' interaction with wild-type and chimeric melanocortin receptors" Protein, 2007, 69(1), pp. 83-96.

Al-Obeidi et al, "Potent and Prolonged Acting Cyclic Lactam Analogues of a-Melanotropin: Design Based on Molecular Dynamics" J. Med. Chem. (1989) vol. 32 No. 12, pp. 2555-2561.

Al-Obeidi et al., "Potent and Prolonged Acting Cyclic Lactam Analogues of a-Melanotropin: Design Based on Molecular Dynamics" Journal of Medicinal Chemistry (1989) vol. 32, pp. 2555-2561.

Bednarek et al. "Analogs of MTII, Lactam Derivatives of a-Melanotropin, Modified at the N-Terminus, and Their Selectivity at Human Melanocortin Receptors 3, 4, and 5" Biochemical and Biophysical Research Communications (1999) vol. 261, pp. 209-213.

Bednarek et al. "Structure-function studies on the cyclic peptide MT-II, lactam derivative of a-melanotropin" Peptides (1999) vol. 20, pp. 401-409.

Brennan et al., "Drug Insight: the role of leptin in human physiology and pathophysiology-emerging clinical applications" Nature Reviews Endocrinology (2006) vol. 2, pp. 318-327.

European Search Report for European Application No. EP 14 719 988.9 dated Oct. 25, 2016.

Farooqi et al. "Clinical and Molecular Genetic Spectrum of Congenital Deficiency of the Leptin Receptor" The New England Journal of Medicine (2007) vol. 356, No. 3, pp. 237-247.

Farooqi et al. "Dominant and recessive inheritance of morbid obesity associated with melanocortin 4 receptor deficiency", The Journal of Clinical Investigation (2000) vol. 106, No. 2, pp. 271-279.

Fung et al., "Design of cyclic and other templates for potent and selective peptide a-MSH analogues" Current Opinion in Chemical Biology, 2005, vol. 9 No. 4, pp. 352-358.

Grieco et al. "Further structure-activity studies of lactam deriT:ratives of MT-II and SHU-9119: Their activity and selectivity at human melanocortin receptors 3, 4, and 5" Peptides (2007) vol. 28, pp. 1191-1196.

Grieco et al., "Structure Activity Studies of the Melanocortin Peptides: Discovery of Potent and Selective Affinity Antagonists for the hMC3 and hMC4 Receptors" Journal of Medicinal Chemistry (2002) vol. 45, pp. 5287-5294.

International Search Report and Written Opinion from International Application No. PCT/US2014/028590, dated Aug. 19, 2014.

Kievit et al., "Chronic Treatment with a Melanocortin-4 Receptor Agonist Causes Weight Loss, Reduces Insulin Resistance, and Improves Cardiovascular Function in Diet-Induced Obese Rhesus Macaques" Diabetes, 2013, vol. 62 No. 2, pp. 490-497.

Krude et al. "Severe early-onset obesity, adrenal insufficiency and red hair pigmentation caused by POMC mutations in humans" Nature Genetics, 1998 vol. 19, pp. 155-157.

Lee "The Role of Leptin-Melanocortin System and Human Weight Regulation: Lessons from Experiments of Nature" Annals Academy of Medicine, Jan. 2009, vol. 38 No. 1, pp. 34-44.

Lee et al, "A POMC variant implicates ?-melanocyte-stimulating hormone in the control of human energy balance" Cell Metabolism (2006) vol. 3, Issue 2, pp. 135-140.

Partial Search Report for Application EP18183527.3 mailed Jan. 31, 2019.

Vaisse et al. "Melanocortin-4 receptor mutations are a frequent and heterogeneous cause of morbid obesity", The Journal of Clinical Investigation (2000) vol. 106, No. 2, pp. 253-262.

Xiang et al. "Pharmacological characterization of 30 human melanocortin-4 receptor polymorphisms with the endogenous proopiomelanocortin-derived agonists, synthetic agonists, and the endogenous agouti-related protein antagonist." Biochemistry (2010), No. 49(22), pp. 4583-4600.

Yan et al. "Potent and selective MC-4 receptor agonists based on a novel disulfide scaffold" Bioorganic & Medicinal Chemistry Letters (2005) vol. 15, pp. 4611-4614.

Extended European Search Report for EP18183527.3 dated May 13, 2019.

\* cited by examiner

SEQUENCE LISTING

```
<160> NUMBER OF SEQ ID NOS: 69

<210> SEQ ID NO 1
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa= D-Alanine
<220> FEATURE:
<221> NAME/KEY: MOD_RES
<222> LOCATION: 5
<223> OTHER INFORMATION: Xaa = D-4-Fluorophenylalanine

<400> SEQUENCE: 1
```

```
Arg Cys Xaa His Xaa Arg Trp Cys
1               5
```

<210> SEQ ID NO 2
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-Phenylalanine

<400> SEQUENCE: 2

```
Arg Cys Xaa Pro Xaa Arg Trp Cys
1               5
```

<210> SEQ ID NO 3
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-4-Fluorophenylalanine

<400> SEQUENCE: 3

```
Arg Cys Xaa Pro Xaa Arg Trp Cys
1               5
```

<210> SEQ ID NO 4
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-4-Fluorophenylalanine

```
<400> SEQUENCE: 4

Arg Cys Xaa Pro Xaa Arg Trp Cys
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-4-Fluorophenylalanine

<400> SEQUENCE: 5

Arg Cys Xaa Ser Xaa Arg Trp Cys
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-4-Cyanophenylalanine

<400> SEQUENCE: 6

Arg Cys Xaa Thr Xaa Arg Trp Cys
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
```

```
<222> LOCATION: 5
<223> OTHER INFORMATION: Xaa = D-Phenylalanine

<400> SEQUENCE: 7

Arg Cys Xaa Asn Xaa Arg Trp Cys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-Phenylalanine

<400> SEQUENCE: 8

Arg Cys Xaa Gln Xaa Arg Trp Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-Phenylalanine

<400> SEQUENCE: 9

Arg Cys Xaa Trp Xaa Arg Trp Cys
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Valine
```

```
<220> FEATURE:
<221> NAME/KEY: MOD_RES
<222> LOCATION: 5
<223> OTHER INFORMATION: Xaa = D-Phenylalanine

<400> SEQUENCE: 10

Arg Cys Xaa His Xaa Arg Trp Cys
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Valine
<220> FEATURE:
<221> NAME/KEY: MOD_RES
<222> LOCATION: 5
<223> OTHER INFORMATION: Xaa = D-Phenylalanine

<400> SEQUENCE: 11

Arg Cys Xaa Gln Xaa Arg Trp Cys
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Valine
<220> FEATURE:
<221> NAME/KEY: MOD_RES
<222> LOCATION: 5
<223> OTHER INFORMATION: Xaa = D-Phenylalanine

<400> SEQUENCE: 12

Arg Cys Xaa Pro Xaa Arg Trp Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
```

```
<222> LOCATION: 3
<223> OTHER INFORMATION: Xaa = D-Serine
<220> FEATURE:
<221> NAME/KEY: MOD_RES
<222> LOCATION: 5
<223> OTHER INFORMATION: Xaa = D-Phenylalanine

<400> SEQUENCE: 13

Arg Cys Xaa Pro Xaa Arg Trp Cys
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Phenylalanine

<400> SEQUENCE: 14

Arg Xaa Xaa Xaa Arg Trp Cys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 4
<223> OTHER INFORMATION: Xaa = D-Phenylalanine

<400> SEQUENCE: 15

Arg Xaa Ala Xaa Arg Trp Cys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Protein
      N-term Ac
<220> FEATURE:
```

```
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 4
<223> OTHER INFORMATION: Xaa = D-Phenylalanine

<400> SEQUENCE: 16

Arg Xaa Ala Xaa Arg Trp Cys
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Phenylalanine
<220> FEATURE:
<221> NAME/KEY: MOD_RES
<222> LOCATION: 7
<223> OTHER INFORMATION: Xaa = Homocysteine

<400> SEQUENCE: 17

Arg Cys Xaa Xaa Arg Trp Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Penicillamine
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Phenylalanine
<220> FEATURE:
<221> NAME/KEY: MOD_RES
<222> LOCATION: 7
<223> OTHER INFORMATION: Xaa = Homocysteine

<400> SEQUENCE: 18
```

```
Arg Xaa Xaa Xaa Arg Trp Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-4-Fluorophenylalanine

<400> SEQUENCE: 19

Arg Xaa Xaa Xaa Arg Trp Cys
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 4
<223> OTHER INFORMATION: Xaa = D-Phenylalanine

<400> SEQUENCE: 20

Arg Xaa Pro Xaa Arg Trp Cys
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: MOD_RES
<222> LOCATION: 1
<223> OTHER INFORMATION: Xaa = Norleucine
<220> FEATURE:
<221> NAME/KEY: DOMAIN
<222> LOCATION: (2)...(7)
<223> OTHER INFORMATION: Cyclic
```

```
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 4
<223> OTHER INFORMATION: Xaa = D-Phenylalanine

<400> SEQUENCE: 21

Xaa Xaa Pro Xaa Arg Trp Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic Protein
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 4
<223> OTHER INFORMATION: Xaa = D-Phenylalanine

<400> SEQUENCE: 22

Arg Xaa Pro Xaa Arg Trp Cys
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Protein
      N-term CH3-(CH2)4-C(O)
      C-term NH2
<220> FEATURE:
<221> NAME/KEY: DOMAIN
<222> LOCATION: (1)...(6)
<223> OTHER INFORMATION: Cyclic
<220> FEATURE:
<221> NAME/KEY: MOD_RES
<222> LOCATION: 1
<223> OTHER INFORMATION: Xaa = Homocysteine
<220> FEATURE:
<221> NAME/KEY: MOD_RES
<222> LOCATION: 3
<223> OTHER INFORMATION: Xaa = D-Phenylalanine

<400> SEQUENCE: 23

Xaa Pro Xaa Arg Trp Cys
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Protein
      N-term Benzyl-C(O)
      C-term NH2
<220> FEATURE:
<221> NAME/KEY: DOMAIN
<222> LOCATION: (1)...(6)
```

```
<223> OTHER INFORMATION: Cyclic
<220> FEATURE:
<221> NAME/KEY: MOD_RES
<222> LOCATION: 1
<223> OTHER INFORMATION: Xaa = Homocysteine
<220> FEATURE:
<221> NAME/KEY: MOD_RES
<222> LOCATION: 3
<223> OTHER INFORMATION: Xaa = D-Phenylalanine

<400> SEQUENCE: 24

Xaa Pro Xaa Arg Trp Cys
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Phenylalanine
<220> FEATURE:
<221> NAME/KEY: MOD_RES
<222> LOCATION: 7
<223> OTHER INFORMATION: Xaa = 2,4-Diaminobutyric acid

<400> SEQUENCE: 25

Arg Asp Xaa Xaa Arg Trp Xaa
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Phenylalanine
<220> FEATURE:
<221> NAME/KEY: MOD_RES
<222> LOCATION: 7
<223> OTHER INFORMATION: Xaa = 2,3-Diaminopropionic acid

<400> SEQUENCE: 26

Arg Glu Xaa Xaa Arg Trp Xaa
1               5

<210> SEQ ID NO 27
```

-continued

```
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 4
<223> OTHER INFORMATION: Xaa = D-Phenylalanine
<220> FEATURE:
<221> NAME/KEY: MOD_RES
<222> LOCATION: 7
<223> OTHER INFORMATION: Xaa = 2,3-Diaminopropionic acid

<400> SEQUENCE: 27

Arg Glu Ala Xaa Arg Trp Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = 2,3-Diaminopropionic acid
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Phenylalanine

<400> SEQUENCE: 28

Arg Xaa Xaa Xaa Arg Trp Glu
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = 2,3-Diaminopropionic acid
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
```

```
<222> LOCATION: 4
<223> OTHER INFORMATION: Xaa = D-4-Fluorophenylalanine

<400> SEQUENCE: 29

Arg Xaa Xaa Xaa Arg Trp Glu
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = 2,3-Diaminopropionic acid
<220> FEATURE:
<221> NAME/KEY: MOD_RES
<222> LOCATION: 4
<223> OTHER INFORMATION: Xaa = D-Phenylalanine

<400> SEQUENCE: 30

Arg Xaa Ala Xaa Arg Trp Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Protein
      N-term Ac
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = 2,3-Diaminopropionic acid
<220> FEATURE:
<221> NAME/KEY: MOD_RES
<222> LOCATION: 4
<223> OTHER INFORMATION: Xaa = D-Phenylalanine

<400> SEQUENCE: 31

Arg Xaa Ala Xaa Arg Trp Glu
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: MOD_RES
<222> LOCATION: 1
<223> OTHER INFORMATION: Xaa = Norleucine
<220> FEATURE:
<221> NAME/KEY: DOMAIN
<222> LOCATION: (2)...(7)
<223> OTHER INFORMATION: Cyclic
<220> FEATURE:
```

```
<221> NAME/KEY: MOD_RES
<222> LOCATION: 2
<223> OTHER INFORMATION: Xaa = 2,3-Diaminopropionic acid
<220> FEATURE:
<221> NAME/KEY: MOD_RES
<222> LOCATION: 4
<223> OTHER INFORMATION: Xaa = D-Phenylalanine

<400> SEQUENCE: 32

Xaa Xaa Ala Xaa Arg Trp Glu
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Protein
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = 2,3-Diaminopropionic acid
<220> FEATURE:
<221> NAME/KEY: MOD_RES
<222> LOCATION: 4
<223> OTHER INFORMATION: Xaa = D-Phenylalanine

<400> SEQUENCE: 33

Arg Xaa Ala Xaa Arg Trp Glu
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Protein
      N-term CH3-(CH2)4-C(O)
      C-term NH2
<220> FEATURE:
<221> NAME/KEY: DOMAIN
<222> LOCATION: (1)...(6)
<223> OTHER INFORMATION: Cyclic
<220> FEATURE:
<221> NAME/KEY: MOD_RES
<222> LOCATION: 1
<223> OTHER INFORMATION: Xaa = 2,3-Diaminopropionic acid
<220> FEATURE:
<221> NAME/KEY: MOD_RES
<222> LOCATION: 3
<223> OTHER INFORMATION: Xaa = D-Phenylanine

<400> SEQUENCE: 34

Xaa Ala Xaa Arg Trp Glu
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic Protein
      N-term Benzyl-C(O)
      C-term NH2
<220> FEATURE:
<221> NAME/KEY: DOMAIN
<222> LOCATION: (1)...(6)
<223> OTHER INFORMATION: Cyclic
```

```
<220> FEATURE:
<221> NAME/KEY: MOD_RES
<222> LOCATION: 1
<223> OTHER INFORMATION: Xaa = 2,3-Diaminopropionic acid
<220> FEATURE:
<221> NAME/KEY: MOD_RES
<222> LOCATION: 3
<223> OTHER INFORMATION: Xaa = D-Phenylalanine

<400> SEQUENCE: 35

Xaa Ala Xaa Arg Trp Glu
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = 3-Methylhistidine
<220> FEATURE:
<221> NAME/KEY: MOD_RES
<222> LOCATION: 5
<223> OTHER INFORMATION: Xaa = D-Phenylalanine

<400> SEQUENCE: 36

Arg Cys Xaa Xaa Xaa Arg Trp Cys
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = 1-Methylhistidine
<220> FEATURE:
<221> NAME/KEY: MOD_RES
<222> LOCATION: 5
<223> OTHER INFORMATION: Xaa = D-Phenylalanine

<400> SEQUENCE: 37

Arg Cys Xaa Xaa Xaa Arg Trp Cys
1               5

<210> SEQ ID NO 38
<211> LENGTH: 8
```

```
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-Phenylalanine

<400> SEQUENCE: 38

Arg Cys Xaa Arg Xaa Arg Trp Cys
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-Phenylalanine

<400> SEQUENCE: 39

Arg Cys Xaa Tyr Xaa Arg Trp Cys
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Proline
<220> FEATURE:
<221> NAME/KEY: MOD_RES
<222> LOCATION: 5
<223> OTHER INFORMATION: Xaa = D-Phenylalanine

<400> SEQUENCE: 40
```

Arg Cys Xaa Xaa Xaa Arg Trp Cys
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = 2-Aminotetralin-2-carboxylic acid
<220> FEATURE:
<221> NAME/KEY: MOD_RES
<222> LOCATION: 5
<223> OTHER INFORMATION: Xaa = D-Phenylalanine

<400> SEQUENCE: 41

Arg Cys Xaa Xaa Xaa Arg Trp Cys
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = 2-Amino-3-(quinolin-3-yl)propanoic acid
<220> FEATURE:
<221> NAME/KEY: MOD_RES
<222> LOCATION: 5
<223> OTHER INFORMATION: Xaa = D-Phenylalanine

<400> SEQUENCE: 42

Arg Cys Xaa Xaa Xaa Arg Trp Cys
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:

```
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = 1-Amino-4-phenylcyclohexane-1-carboxylic
      acid
<220> FEATURE:
<221> NAME/KEY: MOD_RES
<222> LOCATION: 5
<223> OTHER INFORMATION: Xaa = D-Phenylalanine

<400> SEQUENCE: 43

Arg Cys Xaa Xaa Xaa Arg Trp Cys
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = 2-Amino-3-(1H-pyrazol-1-yl) propanoic
      acid
<220> FEATURE:
<221> NAME/KEY: MOD_RES
<222> LOCATION: 5
<223> OTHER INFORMATION: Xaa = D-Phenylalanine

<400> SEQUENCE: 44

Arg Cys Xaa Xaa Xaa Arg Trp Cys
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Phenylalanine
<220> FEATURE:
<221> NAME/KEY: MOD_RES
<222> LOCATION: 7
<223> OTHER INFORMATION: Xaa = Penicillamine
```

<400> SEQUENCE: 45

Arg Xaa Xaa Xaa Arg Trp Xaa
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 3
<223> OTHER INFORMATION: Xaa = alpha-Aminoisobutyric acid
<220> FEATURE:
<221> NAME/KEY: MOD_RES
<222> LOCATION: 4
<223> OTHER INFORMATION: Xaa = D-Phenylalanine

<400> SEQUENCE: 46

Arg Xaa Xaa Xaa Arg Trp Cys
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 3
<223> OTHER INFORMATION: Xaa = Sarcosine
<220> FEATURE:
<221> NAME/KEY: MOD_RES
<222> LOCATION: 4
<223> OTHER INFORMATION: Xaa = D-Phenylalanine

<400> SEQUENCE: 47

Arg Xaa Xaa Xaa Arg Trp Cys
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN

```
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 4
<223> OTHER INFORMATION: Xaa = D-Phenylalanine

<400> SEQUENCE: 48

Arg Xaa Val Xaa Arg Trp Cys
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 3
<223> OTHER INFORMATION: Xaa = D-Valine
<220> FEATURE:
<221> NAME/KEY: MOD_RES
<222> LOCATION: 4
<223> OTHER INFORMATION: Xaa = D-Phenylalanine

<400> SEQUENCE: 49

Arg Xaa Xaa Xaa Arg Trp Cys
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 4
<223> OTHER INFORMATION: Xaa = D-Phenylalanine

<400> SEQUENCE: 50

Arg Xaa Gln Xaa Arg Trp Cys
1               5

<210> SEQ ID NO 51
<211> LENGTH: 7
<212> TYPE: PRT
<213> ORGANISM: Artificial Sequence
```

```
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 3
<223> OTHER INFORMATION: Xaa = D-Glutamine
<220> FEATURE:
<221> NAME/KEY: MOD_RES
<222> LOCATION: 4
<223> OTHER INFORMATION: Xaa = D-Phenylalanine

<400> SEQUENCE: 51

Arg Xaa Xaa Xaa Arg Trp Cys
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 4
<223> OTHER INFORMATION: Xaa = D-Phenylalanine
<220> FEATURE:
<221> NAME/KEY: MOD_RES
<222> LOCATION: 7
<223> OTHER INFORMATION: Xaa = D-Penicillamine

<400> SEQUENCE: 52

Arg Xaa Ala Xaa Arg Trp Xaa
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = D-Penicillamine
<220> FEATURE:
<221> NAME/KEY: MOD_RES
<222> LOCATION: 3
<223> OTHER INFORMATION: Xaa = D-Alanine
<220> FEATURE:
```

```
<221> NAME/KEY: MOD_RES
<222> LOCATION: 4
<223> OTHER INFORMATION: Xaa = D-Phenylalanine
<220> FEATURE:
<221> NAME/KEY: MOD_RES
<222> LOCATION: 7
<223> OTHER INFORMATION: Xaa = Homocysteine

<400> SEQUENCE: 53

Arg Xaa Xaa Xaa Arg Trp Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Penicillamine
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Phenylalanine
<220> FEATURE:
<221> NAME/KEY: MOD_RES
<222> LOCATION: 7
<223> OTHER INFORMATION: Xaa = Homocysteine

<400> SEQUENCE: 54

Arg Xaa Xaa Xaa Arg Trp Xaa
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = D-Homocysteine
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = D-Phenylalanine

<400> SEQUENCE: 55

Arg Xaa Xaa Xaa Arg Trp Cys
1               5
```

```
<210> SEQ ID NO 56
<211> LENGTH: 7
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(7)
<223> OTHER INFORMATION: Cyclic
<220> FEATURE:
<221> NAME/KEY: MOD_RES
<222> LOCATION: 2
<223> OTHER INFORMATION: Xaa = Homocysteine
<220> FEATURE:
<221> NAME/KEY: MOD_RES
<222> LOCATION: 3
<223> OTHER INFORMATION: Xaa = D-Proline
<220> FEATURE:
<221> NAME/KEY: MOD_RES
<222> LOCATION: 4
<223> OTHER INFORMATION: Xaa = D-Phenylalanine

<400> SEQUENCE: 56

Arg Xaa Xaa Xaa Arg Trp Cys
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 5
<223> OTHER INFORMATION: Xaa = D-Phenylalanine

<400> SEQUENCE: 57

Arg Cys Val Gln Xaa Arg Trp Cys
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Valine
<220> FEATURE:
<221> NAME/KEY: MOD_RES
<222> LOCATION: 4
<223> OTHER INFORMATION: Xaa = 1-Methylhistidine
<220> FEATURE:
<221> NAME/KEY: MOD_RES
<222> LOCATION: 5
<223> OTHER INFORMATION: Xaa = D-Phenylalanine
```

```
<400> SEQUENCE: 58

Arg Cys Xaa Xaa Xaa Arg Trp Cys
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: MOD_RES
<222> LOCATION: 1
<223> OTHER INFORMATION: Xaa = 3-(1,2,4-Triazol-1-yl)-L-alanine
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 5
<223> OTHER INFORMATION: Xaa = D-Phenylalanine

<400> SEQUENCE: 59

Xaa Cys Ala Gln Xaa Arg Trp Cys
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 5
<223> OTHER INFORMATION: Xaa = D-Phenylalanine

<400> SEQUENCE: 60

Glu Cys Ala His Xaa Arg Trp Cys
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Leucine
<220> FEATURE:
<221> NAME/KEY: MOD_RES
<222> LOCATION: 5
<223> OTHER INFORMATION: Xaa = D-Phenylalanine

<400> SEQUENCE: 61
```

Arg Cys Xaa His Xaa Arg Trp Cys
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Isoleucine
<220> FEATURE:
<221> NAME/KEY: MOD_RES
<222> LOCATION: 5
<223> OTHER INFORMATION: Xaa = D-Phenylalanine

<400> SEQUENCE: 62

Arg Cys Xaa His Xaa Arg Trp Cys
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Tert-leucine
<220> FEATURE:
<221> NAME/KEY: MOD_RES
<222> LOCATION: 5
<223> OTHER INFORMATION: Xaa = D-Phenylalanine

<400> SEQUENCE: 63

Arg Cys Xaa His Xaa Arg Trp Cys
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 4
<223> OTHER INFORMATION: Xaa = 1-Methylhistidine

```
<220> FEATURE:
<221> NAME/KEY: MOD_RES
<222> LOCATION: 5
<223> OTHER INFORMATION: Xaa = D-(2-Napthyl)-alanine

<400> SEQUENCE: 64

Arg Cys Xaa Xaa Xaa Arg Trp Cys
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-(2-Napthyl)-alanine

<400> SEQUENCE: 65

Arg Cys Xaa Gln Xaa Arg Trp Cys
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic Protein
      N-term Ac
      C-term NH2
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-(2-Napthyl)-alanine

<400> SEQUENCE: 66

Arg Cys Xaa Asn Xaa Arg Trp Cys
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic Protein
      N-term Ac
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
```

```
<223> OTHER INFORMATION: Xaa = D-Alanine
<220> FEATURE:
<221> NAME/KEY: MOD_RES
<222> LOCATION: 4
<223> OTHER INFORMATION: Xaa = 1-Methylhistidine
<220> FEATURE:
<221> NAME/KEY: MOD_RES
<222> LOCATION: 5
<223> OTHER INFORMATION: Xaa = D-Phenylalanine

<400> SEQUENCE: 67

Arg Cys Xaa Xaa Xaa Arg Trp Cys
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic Protein
      N-term Ac
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-Phenylalanine

<400> SEQUENCE: 68

Arg Cys Xaa Gln Xaa Arg Trp Cys
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic Protein
      N-term Ac
<220> FEATURE:
<221> NAME/KEY: DOMAIN
<222> LOCATION: (2)...(8)
<223> OTHER INFORMATION: Cyclic
<220> FEATURE:
<221> NAME/KEY: MOD_RES
<222> LOCATION: 3
<223> OTHER INFORMATION: Xaa = D-Alanine
<220> FEATURE:
<221> NAME/KEY: MOD_RES
<222> LOCATION: 5
<223> OTHER INFORMATION: Xaa = D-Phenylalanine

<400> SEQUENCE: 69

Arg Cys Xaa Asn Xaa Arg Trp Cys
1               5
```

PEPTIDE COMPOSITIONS

RELATED APPLICATION

This application continuation of U.S. application Ser. No. 16/216,116, filed Dec. 11, 2018, which is a divisional of U.S. application Ser. No. 14/775,916, filed Sep. 14, 2015, which is a U.S. National Phase Application under 35 U.S.C. § 371 of International Application No. PCT/US2014/028590, filed Mar. 14, 2014, which claims the benefit of U.S. Provisional Application No. 61/790,469, filed Mar. 15, 2013, the contents of which are incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jul. 2, 2014, is named R2054-7002WO_SL.txt and is 30,833 bytes in size.

BACKGROUND OF THE INVENTION

Disorders such as obesity, metabolic syndrome, insulin resistance and diabetes dramatically add to national healthcare costs and can have a severe impact on the quality of life of afflicted individuals, their families and caregivers. The incidence of these disorders is increasing, approaching epidemic proportions.

Accordingly, a need exists for compositions and methods of treating these disorders.

SUMMARY OF THE INVENTION

The present invention relates to polypeptide compounds that are melanocortin-4 receptor (MC4R) modulators and pharmaceutical compositions comprising same.

In a particular embodiment the polypeptide compound is an isolated polypeptide of the following structural Formula (I):

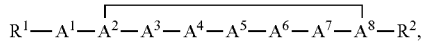

or a pharmaceutically acceptable salt thereof,
wherein:
  $R^1$ is H, or a C1-C6 acyl;
  $R^2$ is $-NR^3R^4$, or $-OR^5$ wherein $R^3$, $R^4$, and $R^5$ are each independently is H or a C1-C6 alkyl;
  $A^1$ is an amino acid residue selected from Arg, Lys, Orn, His, Nle, Phe, Val, Leu, Trp, Tyr, Ala, Ser, Thr, Gln, Asn, Asp, Glu, or TzAla; or
  $A^1$ is a moiety selected from an optionally substituted C1-C12 alkyl, an optionally substituted C6-C18 aryl, an optionally substituted C5-C18 heteroaryl, an aralkyl wherein the aryl portion is an optionally substituted C6-C18 aryl, and the alkyl portion is an optionally substituted C1-C12 alkyl, or a heteroaralkyl, wherein the heteroaryl portion is an optionally substituted C5-C18 heteroaryl, and the alkyl portion is an optionally substituted C1-C12 alkyl;
  $A^2$ and $A^8$ is each independently an amino acid residue selected from Cys, hCys, Pen, Asp, Glu, Lys, Orn, Dbu, or Dpr, wherein $A^2$ and A are pairwise selected so as to be able to form covalent bond between their respective side chains;
  $A^3$ is absent or is an amino acid residue selected from Ala, Tle, Val, Leu, Ile, Cha, Pro, Ser, Thr, Lys, Arg, His, Phe, Gln, Sar, Gly, Asn, Aib, or residue Y, wherein Y is an amino acid selected from amino acids represented by the following structural formulas

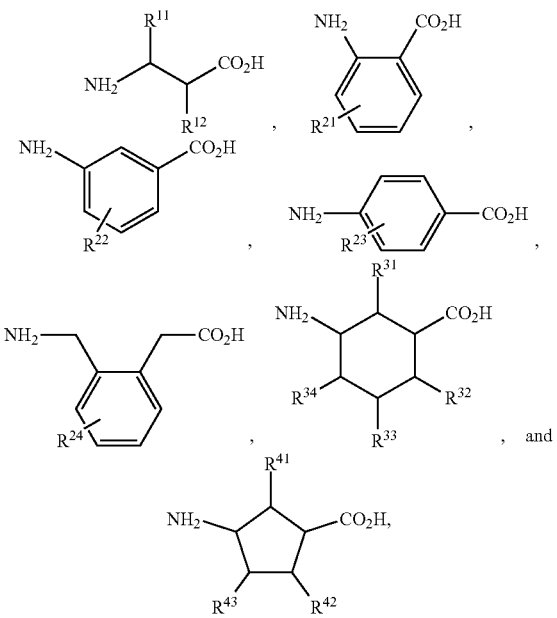

wherein:
  $R^{11}$ and $R^{12}$, each independently, is H, $-CH_3$, phenyl, or benzyl;
  $R^{21}$, $R^{22}$, $R^{23}$, and $R^{24}$, each independently is H, $-CH_3$, $-CF_3$, phenyl, benzyl, F, Cl, Br, I, $-OCH_3$, or $-OH$;
  $R^{31}$, $R^{32}$, $R^{33}$, $R^{34}$, $R^{41}$, $R^{42}$, and $R^{43}$, each independently is H, $-CH_3$, $-CF_3$, phenyl, benzyl, F, Cl, Br, I, $-OCH_3$, or $-OH$;
  $A^4$ is absent or is an amino acid residue selected from Atc, Ala, QAla, Aib, Sar, Ser, Thr, Pro, Hyp, Asn, Gln, an optionally substituted His, Trp, Tyr, Lys, Arg, sChp, or residue X, where the X is an amino acid selected from amino acids represented by the following structural formulas:

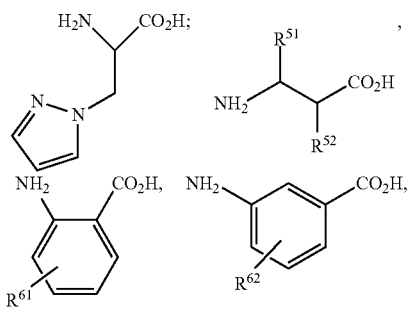

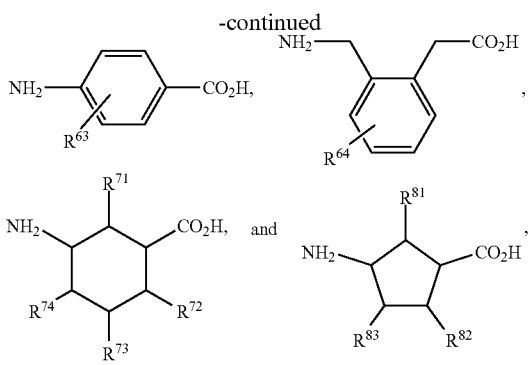

wherein:
- $R^{51}$ and $R^{52}$, each independently, is H, —$CH_3$, phenyl, or benzyl;
- $R^{61}$, $R^{62}$, $R^{63}$, and $R^{64}$, each independently is H, —$CH_3$, —$CF_3$, phenyl, benzyl, F, Cl, Br, I, —$OCH_3$, or —OH;
- $R^7$, $R^{72}$, $R^{73}$, $R^{74}$, $R^{81}$, $R^2$, and $R^{83}$, each independently is H, —$CH_3$, —$CF_3$, phenyl, benzyl, F, Cl, Br, I, —$OCH_3$, or —OH;
- $A^5$ is an optionally substituted Phe, optionally substituted 1-Nal, or an optionally substituted 2-Nal;
- $A^6$ is Arg; and
- $A^7$ is Trp, wherein any amino acid residue is either in L- or in D-configuration, provided that:
1) $A^3$ and $A^4$ are not both absent;
2) when $A^4$ is an amino acid, $A^3$ is not Aib or Gly; and
3) when $A^4$ is His and $A^5$ is a D-Phe or 2-Nal, $A^3$ is not a D-amino acid or L-Ala;
4) when $A^2$ and $A^8$ each is selected from Cys, hCys or Pen, then:
    (a) when $A^4$ is absent, then $A^3$ is not L-His;
    (b) when $A^3$ is absent, then $A^4$ is not L-His; and
    (c) when $A^4$ is His, then $A^3$ is not Glu, Leu, or Lys.

The present invention also relates to a method of treating a disorder responsive to the modulation of MC4R in a subject in need of treatment. The method comprises administering to the subject an effective amount of an MC4R modulator described herein. In a particular embodiment, the disorder responsive to modulation of the MC4R includes type 1 diabetes, type 2 diabetes, obesity, insulin resistance, metabolic syndrome, male erectile dysfunction, female sexual disorder, non-alcoholic fatty liver disease, non-alcoholic steatohepatitis, disorders of substance abuse, including alcoholism feeding disorders, cachexia, inflammation and anxiety.

In certain embodiments, the compounds and compositions of the present invention possess higher selectivity and potency for the MC4R and melanocortin-3 receptor (MC3R) when compared to melanocortin-1 receptor (MC1R). The compounds and compositions of the present invention can reduce or eliminate such undesirable side effects as increase in blood pressure effects, increase in heart rate, undesired effects on sexual arousal, and increase in skin pigmentation.

DETAILED DESCRIPTION OF THE INVENTION

A description of example embodiments of the invention follows.

Glossary

The nomenclature used to define the peptides is that typically used in the art wherein the amino group at the N-terminus appears to the left and the carboxyl group at the C-terminus appears to the right.

As used herein, the term "amino acid" includes both a naturally occurring amino acid and a non-natural amino acid. Unless otherwise indicated, all amino acids and their residues found in the compounds described herein can be either in D or L configuration.

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention.

Unless defined otherwise, all technical and scientific terms used herein have the same meaning as commonly understood by one of ordinary skill in the art to which this invention belongs. All publications, patent applications, patents and other references mentioned herein are incorporated by reference in their entirety.

| Symbol | Meaning |
|---|---|
| Abu | α-aminobutyric acid |
| Ac | acyl group |
| Aib | α-aminoisobutyric acid |
| Ala or A | alanine |
| Arg or R | arginine |
| Asn or N | asparagine |
| Asp or D | aspartic acid |
| Atc | 2-aminotetralin-2-carboxylic acid |
| Cha | β-cyclohexylalanine |
| sChp | 1-amino-4-phenylcyclohexane-1-carboxylic acid |
| Cys or C | cysteine |
| hCys | homocysteine |
| Dbu | 2,4-diaminobutyric acid |
| Dpr | 2,3-diaminopropionic acid |
| Gln or Q | glutamine |
| Glu or E | glutamic acid |
| Gly or G | glycine |
| His or H | histidine |
| Hyp | hydroxyproline |
| Ile or I | isoleucine |
| Leu or L | leucine |
| Lys or K | lysine |
| Met or M | methionine |
| 1-Nal | (1-naphthyl)-alanine |

| Symbol | Meaning |
|---|---|
| 2-Nal | (2-naphthyl)-alanine |
| Nle | norleucine |
| Orn | ornithine |
| Pen | penicillamine |
| Phe or F | phenylalanine |
| Pro or P | proline |
| QAla | 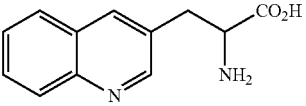 quinolinylalanine or 2-amino-3-(quinolin-3-yl)propanoic acid |
| Sar | sarcosine (N-methylglycine) |
| Ser or S | Serine |
| Tle | tert-leucine (tert-butyl glycine) |
| TzAla | 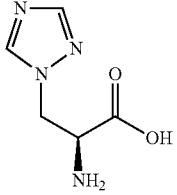 3-(1,2,4-triazol-1-yl)-L-Ala |
| Thr or T | threonine |
| Trp or W | tryptopham |
| Tyr or Y | tyrosine |
| Val or V | valine |
| BHA | benzhydrylamine |
| Boc | tert-butyloxycarbonyl |
| But | tertiary butyl |
| DIPEA | N,N-diisopropylethylamine |
| DTT | dithiothreitol |
| Fmoc | fluorenylmethyloxycarbonyl |
| HBTU | 2-(1H-benzotriazole-1-yl)-1,1,3,3-tetramethyluronium hexafluorophosphate |
| MCR4 | melanocortin-4 receptor |
| Mtt | 4-methyltrityl |
| NMP | N-methylpyrrolidone |
| OBut | tertiary butoxy |
| OPip | 2-phenylisopropyl |
| Pbf | 2,2,4,6,7-pentamethyldihydrobenzofuran-5-sulfonyl |
| Trt | trityl |
| TIS | triisopropylsilane |
| TFA | trifluoroacetic acid |

Unless otherwise indicated, all abbreviations (e.g. Ala) of amino acids in this disclosure refer to amino acid residues, i.e. stand for the structure of —NH—C(R)(R')—CO—, wherein R and R' each is, independently, hydrogen or the side chain of an amino acid (e.g., R=CH₃ and R'=H for Ala, or R and R' may be joined to form a ring system).

The designation "Ac" or "NH₂" at a terminus of a polypeptide indicates that the corresponding terminus is acylated or amidated, respectively.

The phrase "a covalent bond between amino acid side chains" means that the side chains of two amino acid residues in question each includes a functional group capable of forming a covalent bond with one another. Examples of such bonds include disulfide bridges formed by Cys, hCys, or Pen side chains, and amide bonds formed by an amino group of one amino acid side chain and a carboxy group of another amino acid side chain, such as, e.g. Asp, Glu, Lys, Orn, Dbu, or Dpr. In example embodiments, amino acids can be pairwise selected so as to be able to form covalent bond between their respective side chains. When a covalent bond between amino acid side chains is formed, the polypeptide may become cyclized. Such a cyclic polypeptide may be indicated either by a structural formula or by using the short-hand notation "co" or "cyclco( )." For example, "-c(Cys-Cys)-" or "-cyclo(Cys-Cys)-" denotes the structure:

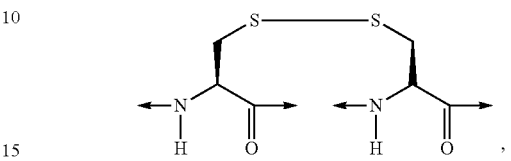

while "-c(Asp-Lys)-" or "-cyclo(Asp-Lys)-" denotes the structure:

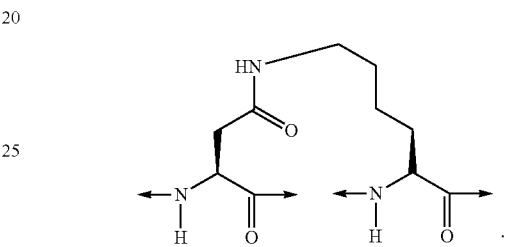

"Alkyl" used alone or as part of a larger moiety such as "hydroxyalkyl", "alkoxyalkyl", "alkylamine" refers to a straight or branched, saturated aliphatic group having the specified number of carbons, typically having 1 to 12 carbon atoms. More particularly, the aliphatic group may have 1 to 8, 1 to 6, or 1 to 4 carbon atoms. This term is exemplified by groups such as methyl, ethyl, n-propyl, isopropyl, n-butyl, isobutyl, tert-butyl, n-hexyl, and the like.

"Haloalkyl" refers to an alkyl group substituted with one or more halogen atoms.

"Halogen" and "halo" refer to fluoro, chloro, bromo or iodo.

"Cyano" refers to the group —CN.

"Ph" refers to a phenyl group.

"Carbonyl" refers to a divalent —C(O)— group.

"Aryl" used alone or as part of a larger moiety as in "aralkyl" refers to an aromatic carbocyclic group of from 6 to 18 carbon atoms having a single ring or multiple condensed rings. The term "aryl" also includes aromatic carbocycle(s) fused to cycloalkyl or heterocycloalkyl groups. Examples of aryl groups include phenyl, benzo[d][1,3]dioxole, naphthyl, phenanthrenyl, and the like.

"Aryloxy" refers to an —OAr group, wherein O is an oxygen atom and Ar is an aryl group as defined above.

"Aralkyl" refers to an alkyl having at least one alkyl hydrogen atom replaced with an aryl moiety, such as benzyl, —(CH₂)₂phenyl, —(CH₂)₃phenyl, —CH(phenyl)₂, and the like.

"Heteroaryl" used alone or a part of a larger moiety as in "heteroaralkyl" refers to a 5 to 18 membered monocyclic, bicyclic or tricyclic heteroaromatic ring system, containing one to four ring heteroatoms independently selected from nitrogen, oxygen and sulfur. The term "heteroaryl" also includes heteroaromatic ring(s) fused to cycloalkyl or heterocycloalkyl groups. Particular examples of heteroaryl groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 1,2,3,4-tetrahydroquinolyl, 1,2,3,4-tetrahydroisoquinolyl, purinyl, pteridinyl, carbazolyl, xanthenyl, benzoquinolyl, and the like.

"Heteroaralkyl" refers to an alkyl having at least one alkyl hydrogen atom replaced with a heteroaryl moiety, such as —CH2-pyridinyl, —CH2-pyrimidinyl, and the like.

"Alkoxy" refers to the group —O—R where R is "alkyl", "cycloalkyl", "alkenyl", or "alkynyl". Examples of alkoxy groups include for example, methoxy, ethoxy, ethenoxy, and the like.

"Hydroxyalkyl" and "alkoxyalkyl" are alkyl groups substituted with hydroxyl and alkoxy, respectively.

"Amino" means —NH$_2$; "alkylamine" and "dialkylamine" mean —NHR and —NR$_2$, respectively, wherein R is an alkyl group. "Cycloalkylamine" and "dicycloalkylamine" mean —NHR and —NR$_2$, respectively, wherein R is a cycloalkyl group. "Cycloalkylalkylamine" means —NHR wherein R is a cycloalkylalkyl group. "[Cycloalkylalkyl][alkyl]amine" means —N(R)$_2$ wherein one R is cycloalkylalkyl and the other R is alkyl.

"Acyl" refers to R"—C(O)—, where R" is H, alkyl, substituted alkyl, heteroalkyl, substituted heteroalkyl, alkenyl, substituted alkenyl, aryl, alkylaryl, or substituted alklyaryl, and is indicated in the general formula of a particular embodiment as "Ac".

Suitable substituents for "alkyl", "aryl", or "heteroaryl", etc., are those which will form a stable compound of the invention. Examples of suitable substituents are those selected from the group consisting of halogen, —CN, —OH, —NH$_2$, (C$_1$-C$_4$)alkyl, (C$_1$-C$_4$)haloalkyl, aryl, heteroaryl, (C$_3$-C$_7$)cycloalkyl, (5-7 membered) heterocycloalkyl, —NH(C$_1$-C$_6$)alkyl, —N((C$_1$-C$_6$)alkyl)$_2$, (C$_1$-C$_6$)alkoxy, (C$_1$-C$_6$)alkoxycarbonyl, —CONH$_2$, —OCONH$_2$, —NHCONH$_2$, —N(C$_1$-C$_6$)alkylCONH$_2$, —N(C$_1$-C$_6$)alkylCONH(C$_1$-C$_6$)alkyl, —NHCONH(C$_1$-C$_6$)alkyl, —NHCON((C$_1$-C$_6$)alkyl)$_2$, —N(C$_1$-C$_6$)akylCON((C$_1$-C$_6$)alkyl)$_2$, —NHC(S)NH$_2$, —N(C$_1$-C$_6$)alkylC(S)NH$_2$, —N(C$_1$-C$_6$)alkylC(S)NH(C$_1$-C$_6$)alkyl, —NHC(S)NH(C$_1$-C$_6$)alkyl, —NHC(S)N((C$_1$-C$_6$)alkyl)$_2$, —N(C$_1$-C$_6$)alkylC(S)N((C$_1$-C$_6$)alkyl)$_2$, —CONH(C$_1$-C$_6$)alkyl, —OCONH(C$_1$-C$_6$)alkyl —CON((C$_1$-C$_6$)alkyl)$_2$, —C(S)(C$_1$-C$_6$)alkyl, —S(O)$_p$(C$_1$-C$_6$)alkyl, —S(O)$_p$NH$_2$, —S(O)$_p$NH(C$_1$-C$_6$)alkyl, —S(O)$_p$N((C$_1$-C$_6$)alkyl)$_2$, —CO(C$_1$-C$_6$)alkyl, —OCO(C$_1$-C$_6$)alkyl, —C(O)O(C$_1$-C$_6$)alkyl, —OC(O)O(C$_1$-C$_6$)alkyl, —C(O)H or —CO$_2$H. More particularly, the substituents are selected from halogen, —CN, —OH, —NH$_2$, (C$_1$-C$_4$)alkyl, (C$_1$-C$_4$)haloalkyl, (C$_1$-C$_4$)alkoxy, phenyl, and (C$_3$-C$_7$)cycloalkyl. Within the framework of this invention, said "substitution" is also meant to encompass situations where a hydrogen atom is replaced with a deuterium atom. p is an integer with a value of 1 or 2.

Suitable substituents on a substituted Phe include one to five substituents on any aromatic carbons, the substituents being selected from F, Cl, Br, I, —CH$_3$, —OH, —CN, amine, —NO$_2$, or —OCH$_3$. Examples include Phe(2'-F), Phe(2'-Cl), Phe(2'-Br), Phe(2'-I), Phe(2'-CN), Phe(2'-CH$_3$), Phe(2'-OCH$_3$), Phe(2'-CF$_3$), Phe(2'-NO$_2$), Phe(3'-F), Phe(3'-Cl), Phe(3'-Br), Phe(3'-I), Phe(3'-CN), Phe(3'-CH$_3$), Phe(3'-OCH$_3$), Phe(3'-CF$_3$), Phe(3'-NO$_2$), Phe(4'-F), Phe(4'-Cl), Phe(4'-Br), Phe(4'-I), Phe(4'-CN), Phe(4'-CH$_3$), Phe(4'-OCH$_3$), Phe(4'-CF$_3$), Phe(4'-NO$_2$), Phe(4'-t-Bu), Phe(2',4'-diF), Phe(2',4'-diCl), Phe(2',4'-diBr), Phe(2',4'-diI), Phe(2',4'-di-CN), Phe(2',4'-di-CH$_3$), Phe(2',4'-di-OCH$_3$), Phe(3',4'-diF), Phe(3',4'-diCl), Phe(3',4'-diBr), Phe(3',4'-diI), Phe(3',4'-di-CN), Phe(3',4'-di-CH$_3$), Phe(3',4'-di-OCH$_3$), Phe(3',5'-diF), Phe(3',5'-diCl), Phe(3',5'-diBr), Phe(3',5'-diI), Phe(3',5'-di-CN), Phe(3',5'-diCH$_3$), Phe(3',5'-di-OCH$_3$), or Phe(3',4',5'-triF).

Suitable substituents on a substituted His include one to three substituents on any substitutable ring atom, the substituents being selected from F, Cl, Br, I, —CH$_3$, —OH, —CN, amine, —NO$_2$, benzyl, or —OCH$_3$. Examples include 1-Methyl-Histidine and 3-Methyl-Histidine.

Designation "(amino acid)$_n$" means that an amino acid is repeated n times. For example, designation "(Pro)$_2$" or "(Arg)$_3$," mean that proline or arginine residues are repeated, respectively, two or three times.

Pharmaceutically acceptable salts of the polypeptide compounds disclosed herein are included in the present invention. For example, an acid salt of a compound containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, triethiodide, and trifluoroacetate salts.

Salts of the compounds containing an acidic functional group can be prepared by reacting with a suitable base. Such a pharmaceutically acceptable salt can be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

The disclosed compounds can be administered to the subject in conjunction with an acceptable pharmaceutical carrier as part of a pharmaceutical composition. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington $\overline{s}$ Pharmaceutical Sciences, Mack Publishing Company, Easton, PA Suitable pharmaceutical carriers for parenteral administration include, for example, sterile water, physiological saline, bacteriostatic saline (saline containing about 0.9% mg/ml benzyl alcohol), phosphate-buffered saline, Hank s solution, Ringer s -lactate and the like. Methods for encapsulating compositions (such as in a coating of hard gelatin or cyclodextrasn) are known in the art (Baker, et al., "Controlled Release of Biological Active Agents", John Wiley and Sons, 1986).

As used herein, the phrase "a disorder responsive to the modulation of the melanocortin-4 receptor" refers to any disorder that can be treated by activation (agonizing) or inhibition of MC4R. Examples of such disorders will be described in detail below.

As used herein, the term "modulator" refers to compounds which interact with the target receptor and affects its biological function. Examples of modulators include full agonists, partial agonists, neutral antagonists, and inverse agonists.

As used herein, the term "agonist" refers to any chemical compound, either naturally occurring or synthetic, that, upon interacting with (e.g., binding to) its target, here, MC4R, raises the signaling activity of MC4R above its basal level. An agonist can be a superagonist (i.e. a compound that is capable of producing a greater maximal response than the endogenous agonist for the target receptor, and thus has an efficacy of more than 100%), a full agonist (i.e. a compound that elicits a maximal response following receptor occupation and activation) or a partial agonist (i.e. a compounds that can activate receptors but are unable to elicit the maximal response of the receptor system). Examples of MC4R agonists will be described in detail below.

As used herein, the term "antagonist" refers to any chemical compound, that, upon interacting with (e.g., binding to) its target, here, MC4R, blocks, in a dose dependent manner, the signaling activity of an agonist compound with the MC4R.

As used herein, the term "inverse agonist" refers to any chemical compound, that, upon interacting with (e.g., binding to) its target, here, MC4R, decreases, in a dose dependent manner, the basal level of signaling activity of the MC4R.

As used herein, an "effective amount" refers to an amount of a therapeutic agent or a combination of therapeutic agents that is therapeutically or prophylactically sufficient to treat the target disorder. Examples of effective amounts typically range from about 0.0001 mg/kg of body weight to about 500 mg/kg of body weight. An example range is from about 0.0001 mg/kg of body weight to about 500 mg/kg. For example, the effective amount can range from about 0.005 mg/kg to about 500 mg/kg. In other examples, the range can be from about 0.0001 mg/kg to about 5 mg/kg. In still other examples, effective amounts range from about 0.01 mg/kg of body weight to 50 mg/kg of body weight, or from 0.01 mg/kg body weight to 20 mg/kg of body weight.

As used herein, the term "subject" refers to a mammal, preferably a human, but can also mean an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein, the term "second agent" includes any active pharmaceutical ingredient (API) that, in combination with a peptide described herein, enhances the therapeutic effect produced by a peptide described herein alone or shows synergy with a peptide described herein (i.e. shows the combined effect that is greater than the additive effect). As used herein, "an enhanced therapeutic effect" includes an improved therapeutic profile other than synergy. Examples of enhanced therapeutic effects include lowered effective dose of a peptide described herein, prolonged therapeutic window of a peptide described herein, etc. One or more second agents can be administered. Examples of second agents will be described in detail below.

A second agent can be administered before, simultaneously with, or after the administration of a peptide described herein. Accordingly, a peptide described herein and a second agent can be administered together in a single formulation or can be administered in separate formulations, e.g., either simultaneously or sequentially. For example, if a peptide described herein and a second agent are administered sequentially in separate compositions, a peptide described herein can be administered before or after a second therapeutic agent. In addition, a peptide described herein and a second agent may or may not be administered on similar dosing schedules. For example, a peptide described herein and a second therapeutic agent may have different half-lives and/or act on different time-scales such that a peptide described herein is administered with greater frequency than the second therapeutic agent or vice-versa. Finally, a peptide described herein can be followed by a second agent, which further enhances therapeutic efficacy, as a result of the consecutive application of both therapeutic agents. Either a peptide described herein or a second agent can be administered acutely or chronically.

An effective amount can be achieved in the methods or compositions of the invention by co-administering a first amount of a compound having an MC4R modulator activity or a pharmaceutically acceptable salt thereof and a second amount of at least one second agent. In one embodiment, a peptide described herein and second agent are each administered in a respective effective amount (i.e., each in an amount which would be therapeutically effective if administered alone). In another embodiment, a peptide described herein and a second agent are each administered in an amount which alone does not provide a therapeutic effect (a sub-therapeutic dose). In yet another embodiment, a peptide described herein can be administered in an effective amount, while the second agent is administered in a sub-therapeutic dose. In still another embodiment, a peptide described herein can be administered in a sub-therapeutic dose, while the second agent is administered in an effective amount. In example embodiment, a combination of a peptide described herein and a second agent exhibits enhanced therapeutic effect or synergy compared to either a peptide described herein or a second agent alone.

The presence of a synergistic effect can be determined using suitable methods for assessing drug interaction. Suitable methods include, for example, the Sigmoid-Emax equation (Holford, N. H. G. and Scheiner, L. B., *Clin. Pharmacokinet.* 6: 429-453 (1981)), the equation of Loewe additivity (Loewe, S. and Muischnek, H., Arch. Exp. Pathol. Pharmacol. 114: 313-326 (1926)), and the median-effect equation (Chou, T. C. and Talalay, P., *Adv. Enzyme Regul.* 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

As used herein "treating" includes achieving, partially or substantially, delaying, inhibiting or preventing the progression of clinical indications related to the target disorder. For example, "treating" includes achieving, partially or substantially, one or more of the following results: partially or totally reducing the body weight (as measured, for example, by a body mass index, BMI); ameliorating or improving a clinical symptom or indicators associated with obesity, such as type-II diabetes, pre-diabetic condition, blood level of haemoglobin A1C (Hb1Ac) above 6%, hyperinsulimenia, hyperlipidemia, insulin insensitivity, glucose intolerance etc; delaying, inhibiting or preventing the progression of obesity and obesity related indication; or partially or totally delaying, inhibiting or preventing the onset or development of obesity or obesity related indication. Delaying, inhibiting or preventing the progression of the obesity includes for example, delaying, inhibiting or preventing the progression of a subject having normal weight to obesity. The term "treating" further includes partially or totally reducing the risk for coronary artery disease, stroke, and diabetes (e.g. type 2) associated with the metabolic syndrome as well as ameliorating or improving a clinical symptom or signs of metabolic syndrome associated with metabolic syndrome, such as any one or more of the five indicators listed above. For example, the term "treating" includes delaying, inhibiting or preventing the progression of parameters associated with the metabolic syndrome, including insulin resistance, glucose clearance and parameters of cardiovascular disease including heart rate and blood pressure, joint disease, inflammation, sleep apnea, binge eating and other eating disorders including bulimia, supportive therapy for weight loss surgery and supportive weight loss therapy prior to orthopedic surgery. "Prophylactic treatment" refers to treatment before onset of clinical symptoms of a target disorder to prevent, inhibit or reduce its occurrence.

Disorder Responsive to the Modulation of the MC4R

Examples of disorders responsive to the modulation of MC4R include acute and chronic inflammatory diseases such as general inflammation, inflammatory bowel disease, brain inflammation, sepsis and septic shock; diseases with an autoimmune component such as rheumatoid arthritis, gouty arthritis, and multiple sclerosis; metabolic diseases and medical conditions accompanied by weight gain such as obesity, feeding disorders and Prader-Willi Syndrome; metabolic diseases and medical conditions accompanied by weight loss such as anorexia, bulimia, AIDS wasting, cachexia, cancer cachexia and wasting in frail elderly; diabetes and diabetalogical related conditions and complications of diabetes such as retinopathy; neoplastic proliferation such as skin cancer, and prostate cancer; reproductive or sexual medical conditions such as endometriosis and uterine bleeding in women, sexual dysfunction, erectile dysfunction and decreased sexual response in females; diseases or conditions resulting from treatment or insult to the organism such as organ transplant rejection, ischemia and reperfusion injury, treatment of spinal cord injury and to accelerate wound healing, as well as weight loss caused by chemotherapy, radiation therapy, temporary or permanent immobilization or dialysis; cardiovascular diseases or conditions such as hemorrhagic shock, cardiogenic shock, hypovolemic shock, cardiovascular disorders and cardiac cachexia; pulmonary diseases or conditions such as acute respiratory distress syndrome, chronic obstructive pulmonary disease, asthma and pulmonary fibrosis; to enhance immune tolerance and to combat assaults to the immune system such as those associated with certain allergies or organ transplant rejection; treatment of dermatological diseases and conditions such as psoriasis, skin pigmentation depletion, acne, keloid formation and skin cancer; behavioral, central nervous system or neuronal conditions and disorders such as anxiety, depression, memory and memory dysfunction, modulating pain perception and treating neuropathic pain; conditions and diseases associated with alcohol consumption, alcohol abuse and/or alcoholism; and renal conditions or diseases such as the treatment of renal cachexia or natriuresis. Additional examples include normalizing or homeostatic activities in a subject, including thyroxin release, aldosterone synthesis and release, body temperature, blood pressure, heart rate, vascular tone, brain blood flow, blood glucose levels, bone metabolism, bone formation or development, ovarian weight, placental development, prolactin and FSH secretion, intrauterine fetal growth, parturition, spermatogenesis, sebum and pheromone secretion, neuroprotection and nerve growth as well as modulating motivation, learning and other behaviors. Further examples include binge eating, bulimia or other eating disorders.

In example embodiments, the disorders responsive to the modulation of the MC4R receptor are type 1 diabetes, type 2 diabetes, obesity, insulin resistance, metabolic syndrome, cardiovascular disease, or low density lipoprotein/high density lipoprotein/triglyceride imbalance, non-alcoholic fatty liver disease, and disorders of substance abuse.

In example embodiments, the disorders responsive to the modulation of the MC4R receptor is type 1 diabetes, type 2 diabetes, obesity, insulin resistance or metabolic syndrome.

Obesity

As used herein, the term "obese" refers to a subject having a body mass index (BMI) of about 30 kg/m$^2$ or higher, e.g., a BMI of 25, 26, 27, 28, 29, 30, 31, 32, 33, 34, 35, 36, 37 kg/m$^2$, or more. In particular embodiments, an obese subject has a BMI within the ranges defined as "obese" by the Center for Disease Control. See, URL http://www.cdc.gov/obesity/defining.html, last accessed on Oct. 28, 2011. For example, in some embodiments, an adult who has a BMI>=30.0 kg/m$^2$ is obese.

Diabetes and Related Disorders

In example embodiments, subjects to be treated by the methods provided by the invention have or are at increased risk for developing diabetes related disorders. "Diabetes-related disorders," refers to diabetes (including type 1 (OMIM 222100) and type 2 (OMIM 125853)), insulin resistance, and metabolic syndrome.

In example embodiments, the subject to be treated has diabetes (type 1 or type 2), insulin resistance, or metabolic syndrome. In example embodiments, the disorder is diabetes, e.g. type 2 diabetes. In example embodiments, the subject has, or is at increased risk for developing, type 2 diabetes as defined by the World Health Organization and the International Diabetes Federation in "Definition and diagnosis of diabetes mellitus and intermediate hyperglycaemia," published in 2006, which is incorporated by reference in its entirety. In example embodiments, a diabetic subject exhibits a fasting plasma glucose of >=126 mg/dL or a 2-hour plasma glucose (2 hours after oral administration of 75 glucose)>=200 mg/dL. In example embodiments a diabetic or pre-diabetic subject exhibits elevated levels of glycated hemoglobin, e.g., greater than 4.5, 4.6, 4.7, 4.8, 4.9, 5.0, 5.1, 5.2, 5.3, 5.4, 5.5, 5.6, 5.8, 6.0, 6.2, 6.4, 6.6, 6.8, 7.0, 7.2, 7.4, 7.6%, or more of total hemoglobin. In example embodiments, a diabetic or pre-diabetic subject may be identified or further characterized by genetic polymorphisms (including, for example, polymorphisms leading to altered expression levels, e.g., elevated or reduced expression levels and/or variations in coding sequences) in or near one or more of the genes in Table 1, below:

TABLE 1

| Location | Gene/Locus | OMIM No. |
|---|---|---|
| 2q24.1 | GPD2 | 138430 |
| 2q31.3 | NEUROD1 | 601724 |
| 2q36.3 | IRS1 | 147545 |
| 3p25.2 | PPARG | 601487 |
| 3q27.2 | IGF2BP2 | 608289 |
| 4p16.1 | WFS1 | 606201 |
| 5q34-q35.2 | NIDDM4 | 608036 |
| 6p22.3 | CDKAL1 | 611259 |
| 6p21.31 | HMGA1 | 600701 |
| 6q23.2 | ENPP1 | 173335 |
| 7p13 | GCK | 138079 |
| 7q32.1 | PAX4 | 167413 |
| 8q24.11 | SLC30A8 | 611145 |
| 10q25.2-q25.3 | TCF7L2 | 602228 |
| 11p15.1 | KCNJ11 | 600937 |
| 11p15.1 | ABCC8 | 600509 |
| 11p11.2 | MAPK8IP1 | 604641 |
| 12q24.31 | HNF1A | 142410 |
| 13q12.2 | IPF1 | 600733 |
| 13q34 | IRS2 | 600797 |
| 15q21.3 | LIPC | 151670 |
| 17p13.1 | SLC2A4 | 138190 |
| 17q12 | HNF1B | 189907 |
| 17q25.3 | GCGR | 138033 |
| 19p13.2 | RETN | 605565 |
| 19p13.2 | RETN | 605565 |
| 19q13.2 | AKT2 | 164731 |
| 20q12-q13.1 | NIDDM3 | 603694 |
| 20q13.12 | HNF4A | 600281 |
| 20q13.13 | PTPN1 | 176885 |

In example embodiments, additional genes that can be used to identify or further characterize subjects to be treated by the methods provided by the invention include FTO (OMIM 610966), JAZF1 (OMIM 606246) and HHEX (OMIM 604420).

In example embodiments, a subject to be treated by the methods provided by the invention has type I diabetes. In example embodiments, a subject with type I diabetes is characterized by virtue of a C-peptide assay, e.g., fasting C-peptide levels of less than about 1.0 nmol/L, e.g., less than 1.2, 1.1, 1.0, 0.9, 0.8, 0.7, 0.6, 0.5, 0.4 nmol/L, or less, e.g., less than 0.33, 0.25, 0.2, or 0.1 nmol/L. In example embodiments, C-peptide levels are measured after oral glucose challenge (2 hours after oral administration of 75 g of glucose) and an increase of less than 0.54 nmol/L, e.g., less than 0.50, 0.45, 0.40, 0.35, 0.30, 0.25, 0.20, 0.15, or 0.10 nmol/L is detected. Impaired fasting glucose (110-125 mg/dL) or impaired glucose tolerance (2-h glucose post-75-g challenge: 140-199 mg/dL) may be used to identify or further characterize the reduced beta-cell function in subjects with type 1 diabetes. In example embodiments, type 1 diabetics are identified or further characterized by the presence of autoantibodies to islet cell antigens and/or insulin, e.g., autoantibodies directed to 65 kDa of GAD (OMIM 138275) and/or phosphatase-related IA-2 molecule.

Insulin Resistance

In example embodiments, the disorder is "insulin resistance," which may be identified by any means known in the art, and is characterized by a reduced ability of insulin to lower blood glucose levels. In example embodiments, the insulin resistance is identified or further characterized by the presence of one or more polymorphisms (including, for example, polymorphisms leading to altered expression levels, e.g., elevated or reduced expression levels as well as coding sequence variants of gene products, such as proteins) in one or more of the following genes: RETN, PTPN1, TCF1 (OMIM 142410; see, e.g., polymorphism 0011), PPP1R3A (OMIM 600917; see, e.g., polymorphisms 0001, 0003), PTPN1 (OMIM 176885; see, e.g., polymorphism 0001), ENPP1 (OMIM 173335; see, e.g., polymorphism 0006), IRS1 (OMIM 147545; see, e.g., polymorphism 0002), EPHX2 (OMIM 132811; see, e.g., polymorphism 0001), leptin (OMIM 164160, see, e.g., polymorphisms 0001 and 0002), leptin receptor (OMIM 601007, see, e.g., polymorphisms 0001, 0002, 0004, and 0005), or the insulin receptor (INSR, OMIM 147670, see, e.g., polymorphisms 0001-0037).

Metabolic Syndrome

In example embodiments, the disorder is metabolic syndrome. As used herein, the term "metabolic syndrome" refers to a group of symptoms that occur together and increase the risk for coronary artery disease, stroke, and type 2 diabetes. According to the American Heart Association and the National Heart, Lung, and Blood Institute, metabolic syndrome also referred to as Syndrome X) is present if a subject has three or more of the following signs:

1) Blood pressure equal to or higher than 130/85 mmHg;
2) Fasting blood sugar (glucose) equal to or higher than 100 mg/dL;
3) Large waist circumference (length around the waist):
Men—40 inches or more;
Women—35 inches or more;
4) Low HDL cholesterol:
Men—under 40 mg/dL;
Women—under 50 mg/dL;
5) Triglycerides equal to or higher than 150 mg/dL.

Metabolic syndrome can be diagnosed by testing the subject's blood pressure, blood glucose level, HDL cholesterol level, LDL cholesterol level, total cholesterol level, and triglyceride level.

In example embodiments the subject has central obesity (waist circumference >=80 cm for women; >=90 cm for Asian men, including ethnic South and Central Americans, and >=94 cm for all other males), BMI>30 kg/m$^2$, raised triglycerides (>=150 mg/dL, or specific treatment for this lipid abnormality), reduced HDL cholesterol (<40 mg/dL in males, <50 mg/dL in females or specific treatment for this lipid abnormality), raised blood pressure (sBP>=130 mmHg or dBP>=85 mmHg or treatment of previously diagnosed hypertension) or raised fasting plasma glucose (FPG>=100 mg/dL or previous type 2 diabetes diagnosis), including combinations thereof. In example embodiments, the subject to be treated by the methods provided by the invention has or is at increased risk for metabolic syndrome, as defined by the International Diabetes Federation in "The IDF consensus worldwide definition of the metabolic syndrome," published in 2006, which is incorporated by reference in its entirety, i.e., the subject has central obesity (as described above, and/or BMI>30 kg/m$^2$) AND any two of raised triglycerides, reduced HDL cholesterol, raised blood pressure, or raised fasting plasma glucose. In example embodiments, metabolic syndrome is characterized, or further characterized, by the presence of a mutation at a locus selected from 3q27 (see, for example, OMIM 605552) and/or 17p12 (see, for example, OMIM 605572) in the subject.

Disorders Caused by MC4R Mutations

The present invention relates to a method of treating a disorder in a subject suffering from an attenuated response of MC4R to α-melanocortin stimulating hormone (α-MSH). The method comprises administering an effective amount of an agonist of the melanocortin-4 receptor (MC4R). In an example embodiment, the subject is a heterozygous carrier of an MC4R mutation resulting in the attenuated response of MC4R to α-melanocortin stimulating hormone (α-MSH).

Because heterozygous carriers retain an ability to respond to the natural ligand of MC4R, treating MC4R-associated disorders in heterozygous carriers by administration of an MC4R agonist does not rely on the knowledge of the type of the MC4R mutation.

In one example embodiment, the disorder is obesity, for example, MC4R-associated obesity. In another example embodiment, the disorder is metabolic syndrome.

Human MC4R gene (hMC4R) is a well-characterized protein encoded by a genomic sequence having GenBank accession number CH471077. Mutations in the MC4R receptor are an associated cause of severe childhood obesity. The carrier prevalence for MC4R mutations in a juvenile-onset obese population has been noted to be around 2.5% with a highest prevalence of 6% among severe obese children. Humans with MC4R mutations show a more or less similar phenotype as has been described for mice with mutations in the MC4 receptor gene. Those people show clear hyperphagia, hyperinsulinaemia, increased fat mass, accompanied by lean body mass, bone mineral density and linear growth rate, with no changes in cortisol levels, gonadotropin, thyroid and sex steroid levels. In contrast to MC4 receptor deletion, hyperphagia and hyperinsulinaemia tends to subside with age inhuman subjects. Similar to the MC4R knockout mice, the phenotype in heterozygote carriers is intermediate in comparison to homozygote carriers. The exhibited hyperphagia observed upon a test meal is less severe than that observed in people with a leptin deficiency. The severity of MC4 receptor dysfunction seen in assays in vitro can predict the amount of food ingested at a test meal by the subject harboring that particular mutation and correlates with the onset and severity of the obese phenotype. At least 90 different MC4 receptor mutations have been associated with obesity and additional mutations in the MC4 receptor are likely to be discovered, leading to a similar obesity phenotype.

Examples of the MC4R mutations that cause obesity in humans are described in Farooqi et al., *The Journal of Clinical Investigation*, July 2000, vol. 106 (2), pp. 271-279 and Vaisse et al., *The Journal of Clinical Investigation*, July 2000, vol. 106(2), pp. 253-262, the relevant portions of which are incorporated herein by reference.

Additional mutations that potentially cause obesity in humans include, R18H, R18L, S36Y, P48S, V50M, F51L, E61K, I69T, D90N, S94R, G98R, I121T, A154D, Y157S, W174C, G181D, F202L, A219 V, I226T, G231S, G238D, N240S, C271R, S295P, P299L, E308K, I317V, L325F, and 750DelGA, as described in Xiang et al., "Pharmacological characterization of 30 human melanocortin-4 receptor polymorphisms with the endogenous proopiomelanocortin-derived agonists, synthetic agonists, and the endogenous agouti-related protein antagonist." Biochemistry, 2010 Jun. 8; 49(22):4583-600, the relevant portions of which are incorporated herein by reference.

Further examples of mutations that potentially cause obesity in humans are those listed in Online Mendelian Inheritance in Man (OMIM), a database of human genes and genetic disorders, under the accession number 155541 (MC4R) (more precisely, accession nos. 155541.0001-155541.0023) at the URL http://omim.org/entry/155541. Representative examples include 4-BP DEL, NT631; 4-BP INS, NT732; TYR35TER; ASP37VAL; SER58CYS; ILE102SER; ASN274SER; 1-BP INS, 112A; 4-BP DEL, 211CTCT; ILE125LYS; ALA175THR; ILE316SER; TYR287TER; ASN97ASP; 15-BP DEL (delta88-92 codons); and SER127LEU. The relevant portions of the OMIM database are incorporated herein by reference.

In example embodiments, the MC4R mutation results in retention of the MC4R signaling activity.

Mutations in the genomic sequence encoding MC4R can be detected by the methods that are well known to a person of ordinary skill in the art. For example, the genomic sequence can be cloned using nucleotide primers, such as e.g., the primers described in Farooqi et al., The Journal of Clinical Investigation, July 2000, vol. 106 (2), pp. 271-279 and Vaisse et al., The Journal of Clinical Investigation, July 2000, vol. 106(2), pp. 253-262, and the cloned sequence analyzed using commercially available sequencers and software.

Activity of MC4R can be measured by the methods well known to a person of ordinary skill in the art. For example, cells can be transiently transfected with the cloned MC4R DNA, the transfected cells contacted by an agonist of MC4R (e.g. α-MSH), and the intracellular level of cAMP, the secondary messenger of MC4R, measured by an electrochemiluminescence assay described, e.g., in Roubert et al., Journal of Endocrinology (2010) 207, pp. 177-183. A reduction in MC4R signaling can be ascertained by comparing the intracellular level of cAMP produced in response to a given agonist by a wild type MC4R to that produced by a mutant MC4R.

MC4R modulators (e.g. agonists) may also be used to treat patients suffering from other disorders, such as reduced availability of the natural agonists of the MC4R. Example of such patients include individuals heterozygous or homozygous for mutations in the genes important in leptin-dependent pathway (Nature Clinical Practice Endocrinology and Metabolism, 2006; 2; 6; 318 and NEng J Med: 2007; 356; 3; 237), proopiomelanocortin processing (Nature Genetics, 1998, 155; Cell Metabolism, 2006; 3; 135; Annals Acad Med, 2009, 38; 1; 34), or mutations in the genes coding for prohormone convertases.

Modes of Administration

Administration of a compound or pharmaceutically acceptable salt thereof or a composition comprising a compound or pharmaceutical salt of a compound of the invention useful to practice the methods described herein, can be continuous, hourly, four times daily, three time daily, twice daily, once daily, once every other day, twice weekly, once weekly, once every two weeks, once a month, or once every two months, or longer or some other intermittent dosing regimen.

Examples of administration of a compound or composition comprising a compound or pharmaceutical salt of a compound of the invention include peripheral administration. Examples of peripheral administration include oral, subcutaneous, intraperitoneal, intramuscular, intravenous, rectal, transdermal, buccal, sublingual, inhalation, pulmonary, or intranasal forms of administration.

Combination Therapy

A peptide described herein can be used for treatment of any of the disorders responsive to the modulation of MC4R, by administration in combination with one or more other pharmaceutically active compounds ("second agent"). Such combination administration can be by means of a single dosage form which includes one or more peptides described herein and one or more second agents, such single dosage forms include a tablet, capsule, spray, inhalation powder, injectable liquid, or the like. Alternatively, combination administration can be by means of administration of two different dosage forms, with one dosage form containing one or more peptides described herein, and the other dosage form including one or more second agents. In this instance, the dosage forms may be the same or different. Without meaning to limit combination therapies, the following exemplifies certain combination therapies which may be employed.

A peptide described herein can be combined with one or more second agents useful in the treatment of various weight and feeding-related disorders, such as obesity and/or overweight. In particular, a second agent can be an anti-obesity drug that affects energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or gastrointestinal motility. Drugs that reduce energy intake include, in part, various pharmacological agents, referred to as anorectic drugs, which are used as adjuncts to behavioral therapy in weight reduction programs.

Generally, a total dosage of the obesity control agents or medications, when used in combination with one or more peptide described herein can range from 0.1 to 3,000 mg/day, preferably from about 1 to 1,000 mg/day, and more preferably from about 1 to 200 mg/day in single or 2-4 divided doses. The exact dose, however, is determined by the attending clinician and is dependent on such factors as the potency of the compound administered, the age, weight, condition, and response of the patient.

One or more peptides described herein can be combined with one or more second agents useful in the treatment of diabetes.

One or more peptides described herein can in addition or alternatively further be combined with one or more second agents useful in the treatment of diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

Second Agent

The one or more second agents are, for example, selected from:
insulin and insulin analogues;
insulin secretagogues, including sulphonylureas (e.g. glipizide) and prandial glucose regulators (sometimes called "short-acting secretagogues"), such as meglitinides (e.g. repaglinide and nateglinide);
agents that improve incretin action: an incretin, an incretin mimetic, an agents that improves incretin function e.g. GLP-1, GIP; GLP-1 agonists (e.g., exenatide, and liraglutide (VICTOZA)), DPP-4 inhibitors (e.g. vildagliptin, saxagliptin, and sitagliptin)
insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity;
agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators;
agents designed to reduce/slow the absorption of glucose from the intestine, such as alpha-glucosidase inhibitors (e.g. miglitol and acarbose);
agents which antagonize the actions of or reduce secretion of glucagon, such as amylin analogues (e.g. pramlintide);
agents that prevent the reabsorption of glucose by the kidney, such as sodium-dependent glucose transporter 2 (SGLT-2) inhibitors (e.g. dapagliflozin);
agents designed to treat the complications of prolonged hyperglycaemia, such as aldose reductase inhibitors (e.g. epalrestat and ranirestat);
agents used to treat complications related to micro-angiopathies;
anti-dyslipidemia agents, such as HMG-CoA reductase inhibitors (statins, e.g. rosuvastatin) and other cholesterol-lowering agents;
PPARα agonists (fibrates, e.g. gemfibrozil and fenofibrate);
bile acid sequestrants (e.g. cholestyramine);
cholesterol absorption inhibitors (e.g. plant sterols (i.e. phytosterols), synthetic inhibitors);
cholesteryl ester transfer protein (CETP) inhibitors; inhibitors of the ileal bile acid transport system (IBAT inhibitors);
bile acid binding resins;
nicotinic acid (niacin) and analogues thereof;
anti-oxidants, such as probucol;
omega-3 fatty acids;
antihypertensive agents, including adrenergic receptor antagonists, such as beta blockers (e.g. atenolol), alpha blockers (e.g. doxazosin), and mixed alpha/beta blockers (e.g. labetalol);
adrenergic receptor agonists, including alpha-2 agonists (e.g. clonidine);
angiotensin converting enzyme (ACE) inhibitors (e.g. lisinopril), calcium channel blockers, such as dihydropyridines (e.g. nifedipine), phenylalkylamines (e.g. verapamil), and benzothiazepines (e.g. diltiazem);
angiotensin II receptor antagonists (e.g. candesartan); aldosterone receptor antagonists (e.g. eplerenone);
centrally acting adrenergic drugs, such as central alpha agonists (e.g. clonidine); and diuretic agents (e.g. furosemide);
haemostasis modulators, including antithrombotics, such as activators of fibrinolysis;
thrombin antagonists;
factor VIIa inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole);
anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant);
feeding behavior modifying agents, such as orexin receptor modulators and melanin-concentrating hormone (MCH) modulators;
neuropeptide Y (NPY)/NPY receptor modulators;
pyruvate dehydrogenase kinase (PDK) modulators;
serotonin receptor modulators;
leptin/leptin receptor modulators;

ghrelin/ghrelin receptor modulators;
an agent that enhances Beta-cell function;
an agent that stimulates energy expenditure (e.g. beta-adrenergic stimulants, UCP-1 agonists, brown fat modulators and stimulants);
an agent that induces lysis of adipocytes (e.g. an antibody);
nicotine or a nicotine withdrawal aid;
estrogen, a natural or synthetic modulator of an estrogen receptor;
a μ-opioid receptor modulator; and
monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g. toloxatone and amiflamine), or a pharmaceutically acceptable salt thereof.

In an example embodiment, an MC4R agonist and a second agent are administered with the simultaneous, sequential or separate administration of a very low calorie diets (VLCD) or low-calorie diets (LCD).

Isolated Polypeptides of the Present Invention

In an example embodiment, the isolated polypeptides (e.g., agonists of MC4R) are those of Formula (I) or a pharmaceutically acceptable salt thereof:
An isolated polypeptide of the following structural Formula (I):

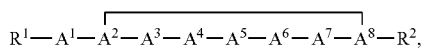

or a pharmaceutically acceptable salt thereof,
wherein:
$R^1$ is H, or a C1-C6 acyl;
$R^2$ is, —$NR^3R^4$, or —$OR^5$ wherein $R^3$, $R^4$, and $R^5$ are each independently is H or a C1-C6 alkyl;
$A^1$ is an amino acid residue selected from Arg, Lys, Orn, His, Nle, Phe, Val, Leu, Trp, Tyr, Ala, Ser, Thr, Gln, Asn, Asp, Glu, or TzAla; or
$A^1$ is a moiety selected from an optionally substituted C1-C12 alkyl, an optionally substituted C6-C18 aryl, an optionally substituted C5-C18 heteroaryl, an aralkyl wherein the aryl portion is an optionally substituted C6-C18 aryl, and the alkyl portion is an optionally substituted C1-C12 alkyl, or a heteroaralkyl, wherein the heteroaryl portion is an optionally substituted C5-C18 heteroaryl, and the alkyl portion is an optionally substituted C1-C12 alkyl;
$A^2$ and $A^8$ is each independently an amino acid residue selected from Cys, hCys, Pen, Asp, Glu, Lys, Orn, Dbu, or Dpr, wherein $A^2$ and A are pairwise selected so as to be able to form covalent bond between their respective side chains;
$A^3$ is absent or is an amino acid residue selected from Ala, Tle, Val, Leu, Ile, Cha, Pro, Ser, Thr, Lys, Arg, His, Phe, Gln, Sar, Gly, Asn, Aib, or residue Y, wherein Y is an amino acid selected from amino acids represented by the following structural formulas

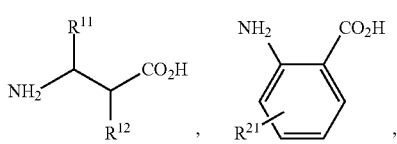

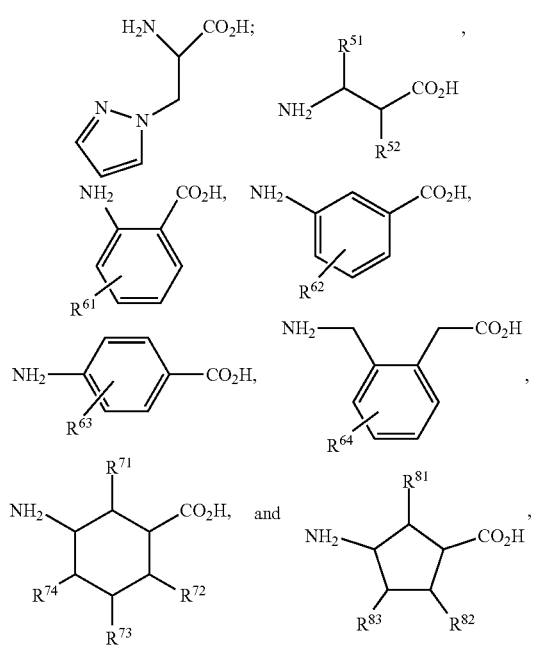

wherein:
$R^{11}$ and $R^{12}$, each independently, is H, —$CH_3$, phenyl, or benzyl;
$R^{21}$, $R^{22}$, $R^{23}$, and $R^{24}$, each independently is H, —$CH_3$, —$CF_3$, phenyl, benzyl, F, Cl, Br, I, —$OCH_3$, or —OH;
$R^{31}$, $R^{32}$, $R^{33}$, $R^{34}$, $R^{41}$, $R^{42}$, and $R^{43}$, each independently is H, —$CH_3$, —$CF_3$, phenyl, benzyl, F, Cl, Br, I, —$OCH_3$, or —OH;
$A^4$ is absent or is an amino acid residue selected from Atc, Ala, QAla, Aib, Sar, Ser, Thr, Pro, Hyp, Asn, Gln, an optionally substituted His, Trp, Tyr, Lys, Arg, sChp, or residue X, where the X is an amino acid selected from amino acids represented by the following structural formulas:

wherein:
$R^{51}$ and $R^{52}$, each independently, is H, —$CH_3$, phenyl, or benzyl;
$R^{61}$, $R^{62}$, $R^{63}$, and $R^{64}$, each independently is H, —$CH_3$, —$CF_3$, phenyl, benzyl, F, Cl, Br, I, —$OCH_3$, or —OH;

$R^7$, $R^{72}$, $R^{73}$, $R^{74}$, $R^{81}$, $R^{12}$, and $R^{83}$, each independently is H, —$CH_3$, —$CF_3$, phenyl, benzyl, F, Cl, Br, I, —$OCH_3$, or —OH;

$A^5$ is an optionally substituted Phe, an optionally substituted 1-Nal, or an optionally substituted 2-Nal;

$A^6$ is Arg; and $A^7$ is Trp, wherein any amino acid residue is either in L- or in D-configuration.

In example embodiments, $A^3$ is absent or is an amino acid residue selected from Ala, Tle, Val, Leu, Ile, Cha, Pro, Ser, Thr, Lys, Arg, His, Phe, Gln, Sar, Gly, Asn, or Aib; and $A^4$ is absent or is an amino acid residue selected from Atc, Ala, QAla, Aib, Sar, Ser, Thr, Pro, Hyp, Asn, Gln, an optionally substituted His, Trp, Tyr, Lys, Arg, sChp, or residue X, where the X is an amino acid represented by the following structural formula

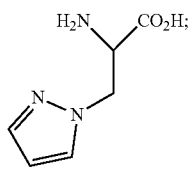 [SMILES: NC(Cn1cccn1)C(=O)O]

Values and preferred values of the remainder of the variables are as defined above and below with respect to Formula (I).

In example embodiments, $A^3$ and $A^4$, each independently, is a residue of an amino acid selected from amino acids represented by the following structural formulas:

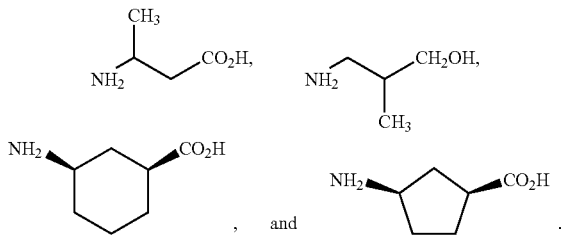

Values and preferred values of the remainder of the variables are as defined above and below with respect to Formula (I).

In example embodiments, $A^3$ and $A^4$ are not both absent. Values and preferred values of the remainder of the variables are as defined above and below with respect to Formula (I).

In example embodiments, when $A^4$ is an amino acid, $A^3$ is not Aib or Gly. Values and preferred values of the remainder of the variables are as defined above with respect to Formula (I).

In example embodiments, when $A^4$ is His and $A^5$ is a D-Phe or 2-Nal, $A^3$ is not a D-amino acid or L-Ala. Values and preferred values of the remainder of the variables are as defined above with respect to Formula (I).

In example embodiments, when $A^2$ and $A^8$ each is selected from Cys, hCys or Pen, then: (a) when $A^4$ is absent, then $A^3$ is not L-His; (b) when $A^3$ is absent, then $A^4$ is not L-His; and (c) when $A^4$ is His, then $A^3$ is not Glu, Leu, or Lys. Values and preferred values of the remainder of the variables are as defined above with respect to Formula (I).

In example embodiments: 1) $A^3$ and $A^4$ are not both absent; 2) when $A^4$ is an amino acid, $A^3$ is not Aib or Gly; and 3) when $A^4$ is His and $A^5$ is a D-Phe or 2-Nal, $A^3$ is not a D-amino acid or L-Ala; 4) when $A^2$ and $A^8$ each is selected from Cys, hCys or Pen, then: (a) when $A^4$ is absent, then $A^3$ is not L-His; (b) when $A^3$ is absent, then $A^4$ is not L-His; and (c) when $A^4$ is His, then $A^3$ is not Glu, Leu, or Lys. Values and preferred values of the remainder of the variables are as defined above with respect to Formula (I).

In another embodiment, the polypeptides of Formula (I), $A^4$ is an L-amino acid. In yet other embodiments, $A^4$ is absent. Values and preferred values of the remainder of the variables are as defined above with respect to Formula (I).

In example embodiments, $A^5$ can be an optionally substituted 1-Nal or an optionally substituted 2-Nal, for example, an optionally substituted D-2-Nal. $A^5$ can be substituted at any of the five aromatic carbons with a substituent selected from F, Cl, Br, I, —$CH_3$, —OH, —CN, amine, —$NO_2$, or —$OCH_3$.

In a further embodiment, the polypeptides of Formula (I), $A^5$ is an optionally substituted D-Phe. $A^5$ can be substituted at any of the five aromatic carbons with a substituent selected from F, Cl, Br, I, —$CH_3$, —OH, —CN, amine, —$NO_2$, or —$OCH_3$. Suitable examples of $A^5$ include, but are not limited to, a D-amino acid residue selected from: Phe, Phe(2'-F), Phe(2'-Cl), Phe(2'-Br), Phe(2'-I), Phe(2'-CN), Phe(2'-$CH_3$), Phe(2'-$OCH_3$), Phe(2'-$CF_3$), Phe(2'-$NO_2$), Phe(3'-F), Phe(3'-Cl), Phe(3'-Br), Phe(3'-I), Phe(3'-CN), Phe(3'-$CH_3$), Phe(3'-$OCH_3$), Phe(3'-$CF_3$), Phe(3'-$NO_2$), Phe(4'-F), Phe(4'-Cl), Phe(4'-Br), Phe(4'-I), Phe(4'-CN), Phe(4'-$CH_3$), Phe(4'-$OCH_3$), Phe(4'-$CF_3$), Phe(4'-$NO_2$), Phe(4'-t-Bu), Phe(2',4'-diF), Phe(2',4'-diCl), Phe(2',4'-diBr), Phe(2',4'-diI), Phe(2',4'-di-CN), Phe(2',4'-di-$CH_3$), Phe(2',4'-di-$OCH_3$), Phe(3',4'-diF), Phe(3',4'-diCl), Phe(3',4'-diBr), Phe(3',4'-diI), Phe(3',4'-di-CN), Phe(3',4'-di-$CH_3$), Phe(3',4'-di-$OCH_3$), Phe(3',5'-diF), Phe(3',5'-diCl), Phe(3',5'-diBr), Phe(3',5'-diI), Phe(3', 5'-di-CN), Phe(3',5'-di$CH_3$), Phe(3',5'-di-$OCH_3$), or Phe(3',4',5'-triF). Values and preferred values of the remainder of the variables are as defined above with respect to Formula (I).

In a further embodiment, the polypeptides of Formula (I), $A^5$ is an optionally substituted D-2-Nal. $A^5$ can be substituted at any of the five aromatic carbons with a substituent selected from F, Cl, Br, I, —$CH_3$, —OH, —CN, amine, —$NO_2$, or —$OCH_3$.

In yet another embodiment, the polypeptides of Formula (I), $A^4$ is His, optionally substituted at any substitutable position with a substituent selected from F, Cl, Br, I, —$CH_3$, —OH, —CN, amine, —$NO_2$, benzyl or —$OCH_3$. Values and preferred values of the remainder of the variables are as defined above with respect to Formula (I).

In a particular embodiment, the compounds of the present invention are those polypeptides of Formula (I) that possess $EC_{50}$ with respect to MC4R from about 0.01 nM to about 10 nM, for example 0.01-3 nM, while possessing the ratio of $EC_{50}(MC1R)/EC_{50}(MC4R)$ of at least 10.

In another embodiment, the polypeptides of the present invention include a polypeptide represented by any one of the following structural formulas:

(SEQ ID NO: 1)
Ac-Arg-Cys-D-Ala-His-D-Phe(p-F)-Arg-Trp-Cys-$NH_2$ (SEQ ID NO: 2)
Ac-Arg-Cys-D-Ala-Pro-D-Phe-Arg-Trp-Cys-$NH_2$ (SEQ ID NO: 3)
Ac-Arg-Cys-D-Ala-Pro-D-Phe(p-F)-Arg-Trp-Cys-$NH_2$

-continued (SEQ ID NO: 4)
Ac-Arg-Cys-D-Ala-Pro-D-Phe(p-F)-Arg-Trp-Cys-NH₂

(SEQ ID NO: 5)
Ac-Arg-Cys-D-Ala-Ser-D-Phe(p-F)-Arg-Trp-Cys-NH₂

(SEQ ID NO: 6)
Ac-Arg-Cys-D-Ala-Thr-D-Phe(p-CN)-Arg-Trp-Cys-NH₂

(SEQ ID NO: 7)
Ac-Arg-Cys-D-Ala-Asn-D-Phe-Arg-Trp-Cys-NH₂

(SEQ ID NO: 8)
Ac-Arg-Cys-D-Ala-Gln-D-Phe-Arg-Trp-Cys-NH₂

(SEQ ID NO: 9)
Ac-Arg-Cys-D-Ala-Trp-D-Phe-Arg-Trp-Cys-NH₂

(SEQ ID NO: 10)
Ac-Arg-Cys-D-Val-His-D-Phe-Arg-Trp-Cys-NH₂

(SEQ ID NO: 11)
Ac-Arg-Cys-D-Val-Gln-D-Phe-Arg-Trp-Cys-NH₂

(SEQ ID NO: 12)
Ac-Arg-Cys-D-Val-Pro-D-Phe-Arg-Trp-Cys-NH₂

(SEQ ID NO: 13)
Ac-Arg-Cys-D-Ser-Pro-D-Phe-Arg-Trp-Cys-NH₂, or a pharmaceutically acceptable salt thereof.

In yet another embodiment, the polypeptides of the present invention include any one of the following structural formulas:

(SEQ ID NO: 14)
Ac-Arg-hCys-D-Ala-D-Phe-Arg-Trp-Cys-NH₂

(SEQ ID NO: 15)
Ac-Arg-hCys-Ala-D-Phe-Arg-Trp-Cys-NH₂

(SEQ ID NO: 16)
Ac-Arg-hCys-Ala-D-Phe-Arg-Trp-Cys-OH (SEQ ID NO: 17)
Ac-Arg-Cys-D-Ala-D-Phe-Arg-Trp-hCys-NH₂

(SEQ ID NO: 18)
Ac-Arg-Pen-D-Ala-D-Phe-Arg-Trp-hCys-NH₂

(SEQ ID NO: 19)
Ac-Arg-hCys-D-Ala-D-Phe(p-F)-Arg-Trp-Cys-NH₂

(SEQ ID NO: 20)
Ac-Arg-hCys-Pro-D-Phe-Arg-Trp-Cys-NH₂

(SEQ ID NO: 21)
Ac-Nle-hCys-Pro-D-Phe-Arg-Trp-Cys-NH₂

(SEQ ID NO: 22)
Arg-hCys-Pro-D-Phe-Arg-Trp-Cys-NH₂

(SEQ ID NO: 23)
CH₃—(CH₂)₄—CO-hCys-Pro-D-Phe-Arg-Trp-Cys-NH₂

(SEQ ID NO: 24)
Benzyl-CO-hCys-Pro-D-Phe-Arg-Trp-Cys-NH₂, or a pharmaceutically acceptable salt thereof.

In a further embodiment, the polypeptides of the present invention include the polypeptide represented by any one of the following structural formulas:

(SEQ ID NO: 25)
Ac-Arg-Asp-D-Ala-D-Phe-Arg-Trp-Dbu-NH₂

(SEQ ID NO: 26)
Ac-Arg-Glu-D-Ala-D-Phe-Arg-Trp-Dpr-NH₂

(SEQ ID NO: 27)
Ac-Arg-Glu-Ala-D-Phe-Arg-Trp-Dpr-NH₂

(SEQ ID NO: 28)
Ac-Arg-Dpr-D-Ala-D-Phe-Arg-Trp-Glu-NH₂

(SEQ ID NO: 29)
Ac-Arg-Dpr-D-Ala-D-Phe(4-F)-Arg-Trp-Glu-NH₂

(SEQ ID NO: 30)
Ac-Arg-Dpr-Ala-D-Phe-Arg-Trp-Glu-NH₂

(SEQ ID NO: 31)
Ac-Arg-Dpr-Ala-D-Phe-Arg-Trp-Glu-OH (SEQ ID NO: 32)
Ac-Nle-Dpr-Ala-D-Phe-Arg-Trp-Glu-NH₂

(SEQ ID NO: 33)
Arg-Dpr-Ala-D-Phe-Arg-Trp-Glu-NH₂

(SEQ ID NO: 34)
CH₃—(CH₂)₄—CO-Dpr-Ala-D-Phe-Arg-Trp-Glu-NH₂

(SEQ ID NO: 35)
Benzyl-CO-Dpr-Ala-D-Phe-Arg-Trp-Glu-NH₂, or a pharmaceutically acceptable salt thereof.

In yet another embodiment, the polypeptides of the present invention include a polypeptide represented by formula (I), wherein $A^4$ is an amino acid residue selected from Atc, Ala, QAla, Aib, Sar, Ser, Thr, Pro, Hyp, Asn, Gln, a substituted His, Trp, Tyr, Lys, Arg, sChp, or residue X. Examples of such peptides include peptides represented b an one of the following structural formulas:

```
                                          (SEQ ID NO: 36)
Ac-Arg-cyclo[Cys-D-Ala-His(3-Me)-D-Phe-Arg-Trp-
Cys]-NH₂;

(SEQ ID NO: 37)
Ac-Arg-cyclo[Cys-D-Ala-His(1-Me)-D-Phe-Arg-Trp-
Cys]-NH₂;

(SEQ ID NO: 9)
Ac-Arg-cyclo[Cys-D-Ala-Trp-D-Phe-Arg-Trp-Cys]-NH₂;

(SEQ ID NO: 8)
Ac-Arg-cyclo[Cys-D-Ala-Gln-D-Phe-Arg-Trp-Cys]-NH₂;
```

(SEQ ID NO: 7)
Ac-Arg-cyclo[Cys-D-Ala-Asn-D-Phe-Arg-Trp-Cys]-NH₂;

(SEQ ID NO: 38)
Ac-Arg-cyclo[Cys-D-Ala-Arg-D-Phe-Arg-Trp-Cys]-NH₂;

(SEQ ID NO: 39)
Ac-Arg-cyclo[Cys-D-Ala-Tyr-D-Phe-Arg-Trp-Cys]-NH₂;

(SEQ ID NO: 40)
Ac-Arg-cyclo[Cys-D-Ala-D-Pro-D-Phe-Arg-Trp-Cys]-NH₂;

(SEQ ID NO: 2)
Ac-Arg-cyclo[Cys-D-Ala-Pro-D-Phe-Arg-Trp-Cys]-NH₂;

(SEQ ID NO: 4)
Ac-Arg-cyclo[Cys-D-Ala-Pro-D-Phe(p-F)-Arg-Trp-Cys]-NH₂;

(SEQ ID NO: 41)
Ac-Arg-cyclo[Cys-D-Ala-Atc-D-Phe-Arg-Trp-Cys]-NH₂;

(SEQ ID NO: 42)
Ac-Arg-cyclo[Cys-D-Ala-QAla-D-Phe-Arg-Trp-Cys]-NH₂;

(SEQ ID NO: 43)
Ac-Arg-cyclo[Cys-D-Ala-sChp-D-Phe-Arg-Trp-Cys]-NH₂;
or (SEQ ID NO: 44)
Ac-Arg-cyclo[Cys-D-Ala-X-D-Phe-Arg-Trp-Cys]-NH₂, or a pharmaceutically acceptable salt thereof.

In example embodiments, the polypeptides of the present invention include a polypeptide represented by any one of the following structural formulas:

(SEQ ID NO: 15)
Ac-Arg-cyclo[hCys-Ala-D-Phe-Arg-Trp-Cys]-NH₂;

(SEQ ID NO: 14)
Ac-Arg-cyclo[hCys-D-Ala-D-Phe-Arg-Trp-Cys]-NH₂;

(SEQ ID NO: 45)
Ac-Arg-cyclo[hCys-D-Ala-D-Phe-Arg-Trp-Pen]-NH₂;

(SEQ ID NO: 26)
Ac-Arg-cyclo[Glu-D-Ala-D-Phe-Arg-Trp-Dpr]-NH₂;

(SEQ ID NO: 27)
Ac-Arg-cyclo[Glu-Ala-D-Phe-Arg-Trp-Dpr]-NH₂;

(SEQ ID NO: 46)
Ac-Arg-cyclo[hCys-Aib-D-Phe-Arg-Trp-Cys]-NH₂;

(SEQ ID NO: 47)
Ac-Arg-cyclo[hCys-Sar-D-Phe-Arg-Trp-Cys]-NH₂;

(SEQ ID NO: 48)
Ac-Arg-cyclo[hCys-Val-D-Phe-Arg-Trp-Cys]-NH₂;

(SEQ ID NO: 49)
Ac-Arg-cyclo[hCys-D-Val-D-Phe-Arg-Trp-Cys]-NH₂;

(SEQ ID NO: 50)
Ac-Arg-cyclo[hCys-Gln-D-Phe-Arg-Trp-Cys]-NH₂;

(SEQ ID NO: 51)
Ac-Arg-cyclo[hCys-D-Gln-D-Phe-Arg-Trp-Cys]-NH₂;

(SEQ ID NO: 52)
Ac-Arg-cyclo[hCys-Ala-D-Phe-Arg-Trp-Pen]-NH₂;

(SEQ ID NO: 53)
Ac-Arg-cyclo[D-Pen-D-Ala-D-Phe-Arg-Trp-hCys]-NH₂;

(SEQ ID NO: 17)
Ac-Arg-cyclo[Cys-D-Ala-D-Phe-Arg-Trp-hCys]-NH₂;

(SEQ ID NO: 54)
Ac-Arg-cyclo[Pen-D-Ala-D-Phe-Arg-Trp-hCys]-NH₂;

(SEQ ID NO: 55)
Ac-Arg-cyclo[D-hCys-D-Ala-D-Phe-Arg-Trp-Cys]-NH₂;

(SEQ ID NO: 20)
Ac-Arg-cyclo[hCys-Pro-D-Phe-Arg-Trp-Cys]-NH₂;
or (SEQ ID NO: 56)
Ac-Arg-cyclo[hCys-D-Pro-D-Phe-Arg-Trp-Cys]-NH₂, or a pharmaceutically acceptable salt thereof.

In another embodiment, the polypeptides of the present invention include polypeptides represented by formula (I), wherein $A^3$ is an amino acid residue selected from Tle, Val, Leu, Ile, Cha, Pro, Ser, Thr, Lys, Arg, His, Phe, Gln, Sar, Gly, Asn, or Aib; and $A^4$ is an amino acid residue selected from Atc, Ala, QAla, Aib, Sar, Ser, Thr, Pro, Hyp, Asn, Gln, a substituted His, Trp, Tyr, Lys, Arg, sChp, or residue X. Examples of such polypeptides are polypeptides represented by any one of the following structural formulas:

(SEQ ID NO: 57)
Ac-Arg-cyclo[Cys-Val-Gln-D-Phe-Arg-Trp-Cys]-NH₂;

(SEQ ID NO: 11)
Ac-Arg-cyclo[Cys-D-Val-Gln-D-Phe-Arg-Trp-Cys]-NH₂;
or (SEQ ID NO: 58)
Ac-Arg-cyclo[Cys-D-Val-His(1-Me)-D-Phe-Arg-Trp-Cys]-NH₂, or a pharmaceutically acceptable salt thereof.

In a further embodiment, the polypeptides of the present invention include a polypeptide represented by any one of the following structural formulas: Ac-TzAla-cyclo[Cys-Ala-Gln-D-Phe-Arg-Trp-Cys]-NH₂; (SEQ ID NO: 59) or Ac-Glu-cyclo[Cys-Ala-His-D-Phe-Arg-Trp-Cys]-NH₂, (SEQ ID NO: 60) or a pharmaceutically acceptable salt thereof.

In yet another embodiment, the polypeptides of the present invention include a polypeptide represented by any one of the following structural formulas:

(SEQ ID NO: 37)
Ac-Arg-cyclo[Cys-D-Ala-His(1-Me)-D-Phe-Arg-Trp-Cys]-NH₂;

(SEQ ID NO: 8)
Ac-Arg-cyclo[Cys-D-Ala-Gln-D-Phe-Arg-Trp-Cys]-NH₂;
or (SEQ ID NO: 7)
Ac-Arg-cyclo[Cys-D-Ala-Asn-D-Phe-Arg-Trp-Cys]-NH₂, or a pharmaceutically acceptable salt thereof.

In a further embodiment, the polypeptides of the present invention include a polypeptide represented by any one of the following structural formulas:

(SEQ ID NO: 61)
Ac-Arg-cyclo[Cys-D-Leu-His-D-Phe-Arg-Trp-Cys]-NH₂;

(SEQ ID NO: 62)
Ac-Arg-cyclo[Cys-D-Ile-His-D-Phe-Arg-Trp-Cys]-NH₂;

```
                                              (SEQ ID NO: 63)
Ac-Arg-cyclo[Cys-D-Tle-His-D-Phe-Arg-Trp-Cys]-NH2;
or
                                              (SEQ ID NO: 10)
Ac-Arg-cyclo[Cys-D-Val-His-D-Phe-Arg-Trp-Cys]-NH2,
``` or a pharmaceutically acceptable salt thereof.

In a further embodiment, the polypeptides of the present invention include a polypeptide represented by any one of the following structural formulas:

```
                                              (SEQ ID NO: 64)
Ac-Arg-cyclo[Cys-D-Ala-His(1-Me)-D-2-Nal-Arg-Trp- Cys]-NH2;

(SEQ ID NO: 65)
Ac-Arg-cyclo[Cys-D-Ala-Gln-D-2-Nal-Arg-Trp-Cys]-

NH2;
or
                                              (SEQ ID NO: 66)
Ac-Arg-cyclo[Cys-D-Ala-Asn-D-2-Nal-Arg-Trp-Cys]-

NH2,
``` or a pharmaceutically acceptable salt thereof.

In a further embodiment, the polypeptides of the present invention include a polypeptide represented by any one of the following structural formulas:

```
                                              (SEQ ID NO: 67)
Ac-Arg-cyclo[Cys-D-Ala-His(1-Me)-D-Phe-Arg-Trp- Cys]-OH;

(SEQ ID NO: 68)
Ac-Arg-cyclo[Cys-D-Ala-Gln-D-Phe-Arg-Trp-Cys]-OH;
or
                                              (SEQ ID NO: 69)
Ac-Arg-cyclo[Cys-D-Ala-Asn-D-Phe-Arg-Trp-Cys]-OH,
``` or a pharmaceutically acceptable salt thereof.

EXEMPLIFICATION

Peptide Synthesis

The peptides of this invention were prepared by conventional solid phase peptide synthesis. The peptide chain was elongated in a step-wise manner starting with its C-terminal end amino acid derivative coupled onto an appropriately selected solid support resin known to be suitable for peptide synthesis. For the synthesis of peptide with a C-terminal amide function, Rink amide MBHA resin was employed as solid support. For the synthesis of peptides with the C-terminal free carboxyl function, resins such as 2-chlorotrityl chloride resin, Wang, or Merrifield resin may be utilized that form an ester bond with the Fmoc-amino acid. Most of these ester linked Fmoc-amino acid-resin types are commercially available from various sources and generally used when feasible.

Synthesis of Disulfide-Cyclized Peptides

The linear derivative of a disulfide cyclic peptides amide was assembled using Fmoc chemistry on a solid-phase peptide synthesizer. The Fmoc-Rink amide resin was placed in a reaction vessel and swollen with NMP. It was then treated with 20% piperidine in NMP for 15 minutes, followed by 3 washes of NMP. The resin was tested for positive Kaiser's test (Kaiser, E, Colescot, R. L., Bossinge, C. D. & Cook, P. I. Anal. Biochem, 1990, 34: 595-598). It was resuspended in NMP and mixed with the required first C-terminal Fmoc-amino acid derivative and HOBt. The coupling reaction was started by the addition of HBTU reagent and DIPEA. After mixing for 2-3 hours, the completion of coupling was confirmed by a negative Kaiser's test on a small aliquot of the resin withdrawn from the reaction mixture. The resin was then washed three times with NMP. Thereafter, the Fmoc group was removed as described earlier and the whole cycle repeated with the second C-terminal Fmoc-amino acid derivative as described. The same cycle of reactions was repeated sequentially with each of the incoming amino acid. The chloranil color test (Vojkovsky, T. Pept. Res., 1995, 8: 236-237) was used instead of Kaiser's test for positive testing of Fmoc deprotection from the proline residue in the peptide sequence as well for testing completion of coupling of an amino acid to proline (a negative chloranil test). In case of peptides with N-terminal acetyl group, the Fmoc deprotected peptide resin was treated for 10 minutes with acetic anhydride and pyridine. The resin after testing negative for Kaiser's test was washed with NMP, dichlromethane and dried in vacuo. The Fmoc-amino acid derivatives were used for the synthesis of these peptides. The trifunctional amino acid derivatives used were the following: Fmoc-Cys(Trt)-OH, Fmoc-Trp(Boc)-OH, Fmoc-Arg(Pbf)-OH, Fmoc-His(Trt)-OH, Fmoc-Asn(Trt)-OH, Fmoc-Gln(Trt)-OH, Fmoc-hCys(Trt)-OH, Fmoc-Pen(Trt)-OH, Fmoc-Tyr(But)-OH, Fmoc-His(1-Me)-OH, Fmoc-His(3-Me)-OH, and Fmoc-Glu(OBut)-OH.

To cleave the peptide off the resin as well as to deprotect the side chain functions, the peptide resin was taken in: 2% TIS/5% water/5% (w/v) DTT/88% TFA. The solution was allowed to mix for 3.5 hours and then filtered. The filtrate was mixed with cold anhydrous ethyl ether. The precipitate was collected by centrifugation. The solvent was decanted and the peptide pellet was re-suspended in fresh ether. The ether workup was repeated two more times. The peptide was dried in vacuo. The crude linear peptide product was diluted to a concentration of 2 mg/mL in 5% acetic acid and 0.5 M iodine/methanol was added dropwise with vigorous stirring until a persistent pale yellow color of the solution was achieved. The solution was stirred for additional 10 minutes. Excess iodine was then quenched by adding 1 M sodium thiosulfate under mixing until the mixture was rendered colorless. The cyclized peptide solution was lyophilized and the crude powder purified by preparative HPLC using a reversed-phase C-18 column. The purified product fractions were pooled and lyophilized. The peptides were analyzed by mass spectrometry using electrospray ionization technique and identified to correct mass.

Synthesis of Lactm-Cyclized Peptides

The cyclic lactam peptides were also synthesized by standard solid phase peptide synthesis methods. For peptides with a C-terminus Dpr, an Fmoc-Dpr(Mtt)-BHA resin was transferred to a solid phase peptide synthesizer reactor. The Fmoc group, was removed as described above and the next Fmoc-protected amino acid, such as for example Fmoc-Trp(Boc)-OH, was coupled to the resin through standard coupling procedures. The Fmoc protective group was removed and the remaining amino acids added individually in the correct sequence, by repeating coupling and deprotection procedures until the amino acid sequence was completed. For glutamic acid, coupling Fmoc-Glu(OPip) was employed. The fully assembled peptide was then acetylated at the N-terminus as per method described earlier for the disulfide series of peptides. The orthogonally protected side chains were then removed. For example, a peptide resin with either an orthogonally protected side chain of Glu as 2-phenylisopropyl (OPip) ester or Dpr as 4-methyltrityl (Mtt), were cleaved by treatment with 1% TFA in dicholoromethane. The deprotected peptide resin was suspended in NMP, and treated with HBTU/DIPEA. After cyclization (a negative Kaiser's test), the peptide-resin was washed with DCM and dried. The cyclic peptide was cleaved from the resin along with any remaining protective groups using trifluoroacetic acid (TFA) in the presence of water and 1,2-ethanedithiol (EDT). The product was collected by precipitation upon the addition of cold anhydrous ether and collected by centrifugation. Final purification was by reversed phase HPLC using a reversed phase C-18 column. The purified peptide collected by lyophilization and analyzed for its mass by mass spectrometry using electron spray methodology.

Examples of the compounds of the present invention are provided in Table 2.

TABLE 2

Example Compounds of the Invention

| Compound | |
|---|---|
| 1 | Ac-Arg-cyclo[Cys-D-Leu-His-D-Phe-Arg-Trp-Cys]-NH$_2$ (SEQ ID NO: 61) |
| 2 | Ac-Arg-cyclo[Cys-D-Ile-His-D-Phe-Arg-Trp-Cys]-NH$_2$ (SEQ ID NO: 62) |
| 3 | Ac-Arg-cyclo[Cys-D-Tle-His-D-Phe-Arg-Trp-Cys]-NH$_2$ (SEQ ID NO: 63) Tle = t-butyl glycine |
| 4 | Ac-Arg-cyclo[Cys-D-Val-His-D-Phe-Arg-Trp-Cys]-NH$_2$ (SEQ ID NO: 10) |
| 5 | Ac-Arg-cyclo[Cys-D-Ala-His(3-Me)-D-Phe-Arg-Trp-Cys]-NH$_2$ (SEQ ID NO: 36) |
| 6 | Ac-Arg-cyclo[Cys-D-Ala-His(1-Me)-D-Phe-Arg-Trp-Cys]-NH$_2$ (SEQ ID NO: 37) |
| 7 | Ac-Arg-cyclo[Cys-D-Ala-Trp-D-Phe-Arg-Trp-Cys]-NH$_2$ (SEQ ID NO: 9) |
| 8 | Ac-Arg-cyclo[Cys-D-Ala-Gln-D-Phe-Arg-Trp-Cys]-NH$_2$ (SEQ ID NO: 8) |
| 9 | Ac-Arg-cyclo[Cys-D-Ala-Asn-D-Phe-Arg-Trp-Cys]-NH$_2$ (SEQ ID NO: 7) |
| 10 | Ac-Arg-cyclo[Cys-D-Ala-Arg-D-Phe-Arg-Trp-Cys]-NH$_2$ (SEQ ID NO: 38) |
| 11 | Ac-Arg-cyclo[Cys-D-Ala-Tyr-D-Phe-Arg-Trp-Cys]-NH$_2$ (SEQ ID NO: 39) |
| 12 | Ac-Arg-cyclo [Cys-D-Ala-D-Pro-D-Phe-Arg-Trp-Cys]-NH$_2$ (SEQ ID NO: 40) |
| 13 | Ac-Arg-cyclo[Cys-D-Ala-Pro-D-Phe-Arg-Trp-Cys]-NH$_2$ (SEQ ID NO: 2) |
| 14 | Ac-Arg-cyclo[Cys-D-Ala-Pro-D-Phe(p-F)-Arg-Trp-Cys]-NH$_2$ (SEQ ID NO: 4) |
| S1 | Ac-Arg-cyclo [Cys-D-Ala-Atc-D-Phe-Arg-Trp-Cys]-NH2 (SEQ ID NO: 41) Atc = [structure: tetrahydronaphthalene with NH$_2$ and CO$_2$H] |
| S2 | Ac-Arg-cyclo [Cys-D-Ala-QAla-D-Phe-Arg-Trp-Cys]-NH2 (SEQ ID NO: 42) QAla = [structure: quinoline with CH$_2$-CH(NH$_2$)-CO$_2$H] |
| S3 | Ac-Arg-cyclo [Cys-D-Ala-sChp-D-Phe-Arg-Trp-Cys]-NH2 (SEQ ID NO: 43) sChp = [structure: phenylcyclohexyl with NH$_2$ and CO$_2$H] |
| S4 | Ac-Arg-cyclo [Cys-D-Ala-X-D-Phe-Arg-Trp-Cys]-NH$_2$ (SEQ ID NO: 44) X = [structure: pyrazolyl-CH$_2$-CH(NH$_2$)-CO$_2$H] |
| 15 | Ac-Arg-cyclo[hCys-Ala-D-Phe-Arg-Trp-Cys]-NH$_2$ (SEQ ID NO: 15) |
| 16 | Ac-Arg-cyclo[hCys-D-Ala-D-Phe-Arg-Trp-Cys ]-NH$_2$ (SEQ ID NO: 14) |
| 17 | Ac-Arg-cyclo[hCys-D-Ala-D-Phe-Arg-Trp-Pen]-NH$_2$ (SEQ ID NO: 45) |
| 18 | Ac-Arg-cyclo[Glu-D-Ala-D-Phe-Arg-Trp-Dpr]-NH$_2$ (SEQ ID NO: 26) |
| 19 | Ac-Arg-cyclo[Glu-Ala-D-Phe-Arg-Trp-Dpr]-NH$_2$ (SEQ ID NO: 27) |
| S5 | Ac-Arg-cyclo[hCys-Aib-D-Phe-Arg-Trp-Cys]-NH$_2$ (SEQ ID NO: 46) |
| S6 | Ac-Arg-cyclo [hCys-Sar-D-Phe-Arg-Trp-Cys]-NH$_2$ (SEQ ID NO: 47) |
| S7 | Ac-Arg-cyclo [hCys-Val-D-Phe-Arg-Trp-Cys]-NH$_2$ (SEQ ID NO: 48) |
| S8 | Ac-Arg-cyclo [hCys-D-Val-D-Phe-Arg-Trp-Cys]-NH$_2$ (SEQ ID NO: 49) |
| S9 | Ac-Arg-cyclo [hCys-Gln-D-Phe-Arg-Trp-Cys]-NH$_2$ (SEQ ID NO: 50) |
| S10 | Ac-Arg-cyclo [hCys-D-Gln-D-Phe-Arg-Trp-Cys]-NH$_2$ (SEQ ID NO: 51) |
| S11 | Ac-Arg-cyclo [hCys-Ala-D-Phe-Arg-Trp-Pen]-NH$_2$ (SEQ ID NO: 52) |

TABLE 2-continued

Example Compounds of the Invention

| Compound | |
|---|---|
| S12 | Ac-Arg-cyclo [D-Pen-D-Ala-D-Phe-Arg-Trp-hCys]-NH$_2$ (SEQ ID NO: 53) |
| S13 | Ac-Arg-cyclo [Cys-D-Ala-D-Phe-Arg-Trp-hCys]-NH$_2$ (SEQ ID NO: 17) |
| S14 | Ac-Arg-cyclo [Pen-D-Ala-D-Phe-Arg-Trp-hCys]-NH$_2$ (SEQ ID NO: 54) |
| S15 | Ac-Arg-cyclo [D-hCys-D-Ala-D-Phe-Arg-Trp-Cys]-NH$_2$ (SEQ ID NO: 55) |
| D1 | Ac-Arg-cyclo [hCys-Pro-D-Phe-Arg-Trp-Cys]-NH$_2$ (SEQ ID NO: 20) |
| D2 | Ac-Arg-cyclo [hCys-D-Pro-D-Phe-Arg-Trp-Cys]-NH$_2$ (SEQ ID NO: 56) |
| 20 | Ac-Arg-cyclo[Cys-Val-Gln-D-Phe-Arg-Trp-Cys]-NH$_2$ (SEQ ID NO: 57) |
| 21 | Ac-Arg-cyclo[Cys-D-Val-Gln-D-Phe-Arg-Trp-Cys]-NH$_2$ (SEQ ID NO: 11) |
| D3 | Ac-Arg-cyclo[Cys-D-Val-His(1-Me)-D-Phe-Arg-Trp-Cys]-NH$_2$, (SEQ ID NO: 58) |
| D4 | Ac-TzAla-cyclo[Cys-Ala-Gln-D-Phe-Arg-Trp-Cys]-NH2 (SEQ ID NO: 59) TzAla = 3-(1,2,4-triazol-1-yl)-L-Ala 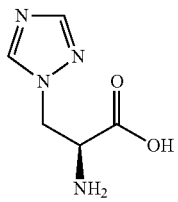 |
| 22 | Ac-Glu-cyclo[Cys-Ala-His-D-Phe-Arg-Trp-Cys]-NH$_2$ (SEQ ID NO: 60) |

Radioligand Binding Assays:

Receptor binding assays for determining the binding constant ($K_d$) or inhibition concentration ($IC_{50}$) for displacing a radio-labeled ligand from the receptor of a cyclic peptide of the invention may be conducted by any means known in the art.

As an example, the cell membrane preparations for a binding assay are prepared from CHO-K1 cells transfected to stably express hMC receptor subtypes 1, 3, 4 or 5. Competitive inhibition of [125I](Tyr2)-(Nle4-D-Phe7)-alpha-MSH ([125I]-NDP-α-MSH binding is carried out in polypropylene 96 well plates. Briefly, the cell membranes (1-10 g protein/well), prepared as described above, is incubated in 50 mM Tris-HCl at pH 7.4 containing 0.2% BSA, 5 mM MgCl2, 1 mM CaCl$_2$) and 0.1 mg/mL bacitracin, with increasing concentrations of the test compound and 0.1-0.3 nM [125I]-NDP-α-MSH for approximately 120 minutes at 37° C. Bound [125I]-NDP-α-MSH ligand is separated from free [125I]-NDP-α-MSH by filtration through GF/C glass fiber filter plates (Unifilter®, Meriden, CT, USA) presoaked with 0.1% (w/v) polyethylenimine (PEI). Filters are washed three times with 50 mM Tris-HCl at pH 7.4 at a temperature of approximately 0-4° C. and then assayed for radioactivity. The binding data are analyzed by computer-assisted non-linear regression analysis.

Cyclic AMP Stimulation Assay

Functional assays to determine agonist or antagonist status of a cyclic peptide of the invention may be conducted by any means known in the art.

Electrochemiluminescence (ECL) Assay

Stimulation of intracellular cyclic AMP (cAMP) levels by the peptides is determined in a dose dependent manner by an electrochemiluminescence (ECL) assay (Meso Scale Discovery, Gaithersburg, MD, USA; referred to hereinafter as "MSD"). Briefly, the CHO-K1 cells stably expressing the hMC receptor subtypes are suspended in RMPI 1640@ assay buffer (RMPI 1640 buffer contains 0.5 mM IBMX, and 0.2% protein cocktail (MSD blocker A)). About 7,000 cells/well of the transgenic CHO-K1 cells stably expressing hMC receptor subtypes 1, 3, 4 or 5 are dispensed in 384-well Multi-Array plates (MSD) containing integrated carbon electrodes and coated with anti-cAMP antibody. Increasing concentrations of the test compounds are added and the cells are incubated for approximately 40 minutes at 37° C. A cell lysis buffer (HEPES-buffered saline solution with MgCl2 and Triton X-100@ at pH 7.3) containing 0.2% protein cocktail and 2.5 nM TAG™ ruthenium-labeled cAMP (MSD) is added and the cells are incubated for approximately 90 minutes at room temperature. At the end of the second incubation period, the read buffer (Tris-buffered solution containing an ECL co-reactant and Triton X-100 at pH 7.8) is added and the cAMP levels in the cell lysates are immediately determined by ECL detection with a Sector Imager 6000 Reader® (MSD). Data are analyzed using a computer-assisted non-linear regression analysis (XL fit; IDBS) and reported as either an EC50 value. The EC50 represents the concentration of an agonist compound needed to obtain 50% of the maximum reaction response, e.g., 50% of the maximum level of cAMP as determined using the assay described above.

cAMP Measurement Assay

Human MC4-R transfected cells are grown to confluence in 96 well plates (plating approximately 250,000 cells per well). The cells are treated in triplicate sets with 0.2 mM isobutylmethylxanthine (IBMX) and graded concentrations of the peptide or alternatively the peptide in the presence of 20 nM NDP-MSH. Cells similarly treated but with only 20 nM NDP-MSH serve as positive controls in a volume of 200 µL. A buffer blank serving as a negative control is also included. After incubation of one hour at 37° C., the cells are lysed by the addition of 50 µL of a cell lysis buffer. Total cAMP accumulated in 250 µL of this incubation medium is quantitated using a commercially available low pH cAMP assay kit (Amersham BioSciences) as per procedure specified by the kit supplier. A peptide showing cAMP accumulation in the range same or higher than the alpha-MSH as positive control is considered to be an agonist. The data for agonist is plotted and curve fitted to determine the EC50 value. A peptide showing accumulation in the same range as the negative control (buffer blank in the absence of alpha-MSH) is ineffective at the test concentration. A peptide showing attenuated accumulation is considered to be an antagonist if there is inhibition in cAMP when alpha-MSH is also present in the assay. Similar assay can be performed with hMC-1R, hMC-3R, and hMC-5R cells.

cAMP Accumulation Measurement via a β-galactosidase (β-Gal) Reporter System

A chemiluminescence readout system that uses an enzyme fragment complementation (EFC) system with β-galactosidase (β-Gal) as the functional reporter system was used. This assay system for various melanocortin receptor systems is commercially available (cAMP Hunter GPCR assay system, Discoverx Corp, Fremont, CA). This assay utilizes the β-Gal enzyme that is split into two complementary portions; EA for Enzyme Acceptor and ED for Enzyme Donor. In the assay, the ED portion fused to cAMP is made to compete with cAMP generated by cells for binding to a cAMP-specific antibody. The EA is then added to form active β-Gal with any unbound ED-cAMP. This active enzyme then converts a chemiluminescent substrate to generate an output signal that is recored on a standard microplate reader.

Briefly, 10000 cells per well are plated overnight and each well (cells incubated with 10 μl assay buffer) is then incubated with 4× serial concentration of the test compound in the cell assay buffer (5 μL) and cAMP antibody reagent (5 μL) for 30 min at 37° C. The cell lysis buffer (20 μL) containing ED-cAMP coupled enzyme fragment and the reporter substrate (Emerald II-Galacton Star, 5:1) is then added and incubated for 60 min at room temperature. Next, 20 μL of EA β-Gal fragment reagent is added. After further incubation for 120 min at room temperature, the chemiluminescence is measured by a plate reader (Envision), and the data used to calculate EC50 values for the test peptide.

The results are presented in Table 3.

TABLE 3

EC50 (nM) values of example compounds of the invention

| | cAMP Assay (EC-50) | | | | Ratios of EC50 values | | |
|---|---|---|---|---|---|---|---|
| Compound | MC1R | MC3R | MC4R | MC5R | MC 1/4 | MC 3/4 | MC 5/4 |
| 1 | 0.47 | 0.79 | 0.70 | 91 | 0.68 | 1.13 | 130 |
| 2 | 0.69 | 0.96 | 1 | 420 | 0.69 | 0.96 | 420 |
| 3 | 1 | 0.7 | 0.7 | 672 | 1 | 1 | 930 |
| 4 | 1.25 | 1.59 | 1.34 | 782 | 0.93 | 1.19 | 584 |
| 5 | 4.1 | 405.8 | 1.15 | 1085 | 4 | 350 | 945 |
| 6 | 30.4 | 4.3 | 0.7 | 467 | 40 | 6 | 662 |
| 7 | 273 | >10 uM | 34 | 259 | 8 | >290 | 7 |
| 8 | 71 | 8.6 | 1.6 | 255 | 40 | 5 | 155 |
| 9 | 248 | 81 | 3 | 1490 | 90 | 30 | 530 |
| 10 | 6.2 | 3.9 | 2.7 | | 2.31 | 1.45 | |
| 11 | 300.9 | >1000 | 45.1 | | 6.67 | >22.2 | |
| 12 | | | | | | | |
| 13 | 280 | >10 uM | 56 | 707 | 5 | >200 | 13 |
| 14 | 169 | >10 uM | 24 | 283 | 7 | >400 | 12 |
| 15 | 4 | 1 | 0.26 | 42 | 15 | 3.8 | 161 |
| 16 | 888 | 3158 | 7.5 | >10000 | 120 | 420 | >1338 |
| 17 | 195 | 233 | 13.7 | 2181 | 15 | 17 | 159 |
| 22 | 1.7 | 9.9 | <0.5 | 1282 | >3 | >20 | >2563 |

While this invention has been particularly shown and described with references to example embodiments thereof, it will be understood by those skilled in the art that various changes in form and details may be made therein without departing from the scope of the invention encompassed by the appended claims.

What is claimed is:

1. An isolated polypeptide of the following structural Formula (I):

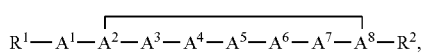

or a pharmaceutically acceptable salt thereof, wherein:

$R^1$ is —H, or a C1-C6 acyl;

$R^2$ is —$NR^3R^4$, or —$OR^5$ wherein $R^3$, $R^4$, and $R^5$ are each independently is-H or a C1-C6 alkyl;

$A^1$ Nle;

$A^2$ and $A^8$ is each independently an amino acid residue selected from Cys, hCys, Glu, or Dpr, wherein $A^2$ and $A^8$ are pairwise selected so as to be able to form a covalent bond between their respective side chains;

A³ is an amino acid residue selected from Ala, Tle, Val, Leu, Ile, Cha, Pro, Ser, Thr, Lys, Arg, His, Phe, Gln, Sar, Gly, Asn, Aib, or A³ is absent, or A³ is residue Y, wherein Y is an amino acid selected from amino acids represented by the following structural formulas

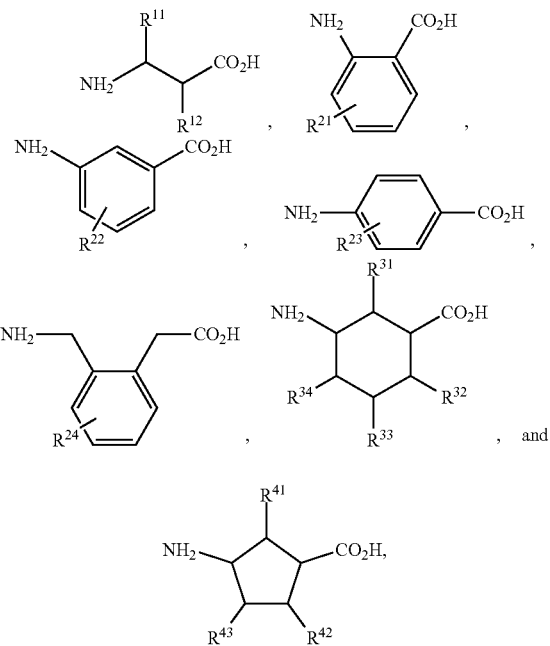

wherein:
$R^{11}$ and $R^{12}$, each independently, is H, —CH₃, phenyl, or benzyl;

$R^{21}$, $R^{22}$, $R^{23}$, and $R^{24}$, each independently is H, —CH₃, —CF₃, phenyl, benzyl, F, Cl, Br, I, —OCH₃, or —OH;

$R^{31}$, $R^{32}$, $R^{33}$, $R^{34}$, $R^{41}$, $R^{42}$, and $R^{43}$, each independently is H, —CH₃, —CF₃, phenyl, benzyl, F, Cl, Br, I, —OCH₃, or —OH;

A⁴ is absent or an optionally substituted His;

A⁵ is an optionally substituted Phe

A⁶ is Arg; and

A⁷ is Trp, wherein any amino acid residue is either in L- or in D-configuration.

2. The polypeptide of claim 1, wherein A⁵ is an optionally substituted D-Phe.

3. A pharmaceutical composition comprising the polypeptide of claim 1 or a pharmaceutically acceptable salt thereof in a pharmaceutically acceptable carrier.

4. The polypeptide of claim 1, represented by any one of the following structural formulas:

Ac-Nle-cyclo[hCys-Pro-D-Phe-Arg-Trp-Cys]-NH₂ (SEQ ID NO: 21); or

Ac-Nle-cyclo[Dpr-Ala-D-Phe-Arg-Trp-Glu]-NH₂ (SEQ ID NO: 32).

5. The polypeptide of claim 1, represented by the following structural formula:

Ac-Nle-cyclo[hCys-Pro-D-Phe-Arg-Trp-Cys]-NH₂ (SEQ ID NO: 21).

6. The polypeptide of claim 1, represented by the following structural formula:

Ac-Nle-cyclo[Dpr-Ala-D-Phe-Arg-Trp-Glu]-NH₂ (SEQ ID NO: 32).

* * * * *